(12) United States Patent
Morimoto

(10) Patent No.: US 9,304,068 B2
(45) Date of Patent: Apr. 5, 2016

(54) CELL COLLECTION APPARATUS, CELL COLLECTING SYSTEM, AND CELL COLLECTING METHOD

(71) Applicant: OLYMPUS CORPORATION, Tokyo (JP)

(72) Inventor: Nobuhiko Morimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/528,508

(22) Filed: Oct. 30, 2014

(65) Prior Publication Data

US 2015/0050690 A1 Feb. 19, 2015

Related U.S. Application Data

(60) Division of application No. 13/686,296, filed on Nov. 27, 2012, now abandoned, which is a continuation of application No. PCT/JP2011/062069, filed on May 26, 2011.

(30) Foreign Application Priority Data

May 28, 2010 (JP) ................................ 2010-122844

(51) Int. Cl.
*A61B 10/00* (2006.01)
*G01N 1/28* (2006.01)
(52) U.S. Cl.
CPC ........ *G01N 1/286* (2013.01); *G01N 2001/2873* (2013.01)
(58) Field of Classification Search
CPC .............................. G01N 33/4833; G01N 1/06
See application file for complete search history.

(56) References Cited

U.S. PATENT DOCUMENTS 3,448,510 A * 6/1969 Johnson, Jr. et al. ........... 29/413
3,932,220 A 1/1976 Liotta
(Continued)

FOREIGN PATENT DOCUMENTS

CN 102918376 A 2/2013
JP 4813260 B1 4/1973
(Continued)

OTHER PUBLICATIONS

Leica Microsystems, "Laser Microdissection Combines High Laser Power and High Repetition Rates Leica LMD6500 & LMD7000", http://www.leica-microsystems.com/products/light-microscopes/life-science-research.
(Continued)

*Primary Examiner* — Jyoti Nagpaul
(74) *Attorney, Agent, or Firm* — Scully, Scott, Murphy & Presser, P.C.

(57) ABSTRACT

In order to pick up a sufficient amount of cells for a genetic test from a section of a biological tissue with a simple structure and a simple operation, provided is a cell collection apparatus comprising: a substrate which is provided to be dividable into a plurality of small pieces along a predetermined dividing line, and which has a flat surface to which a section of a biological tissue can be pasted; a sheet-shaped expandable member to which the substrate can be adhered in a detachable manner, and which is expandable in a direction along the surface; a expansion unit for expanding the expandable member in at least a region adhered with the substrate, in a direction along the surface; and a pickup unit for detaching and picking up the divided small pieces from the expandable member.

12 Claims, 22 Drawing Sheets

(56) References Cited

U.S. PATENT DOCUMENTS

| | | | |
|---|---|---|---|
| 4,647,543 A | 3/1987 | Stöcker | |
| 4,752,347 A * | 6/1988 | Rada | 156/382 |
| 5,998,129 A | 12/1999 | Schutze et al. | |
| 2002/0142412 A1 | 10/2002 | Ogawa et al. | |
| 2002/0197770 A1 | 12/2002 | Irie | |
| 2003/0032082 A1 | 2/2003 | Leclerc | |
| 2004/0014205 A1 | 1/2004 | Banes | |
| 2006/0121596 A1 | 6/2006 | Chaumat | |
| 2010/0050838 A1 | 3/2010 | Noguchi et al. | |

FOREIGN PATENT DOCUMENTS

| | | |
|---|---|---|
| JP | 5586173 A | 6/1980 |
| JP | 10229097 A | 8/1998 |
| JP | 11-148887 | 6/1999 |
| JP | 11163006 A | 6/1999 |
| JP | 2000-504824 | 4/2000 |
| JP | 2002-202229 | 7/2002 |
| JP | 2002-286592 | 10/2002 |
| JP | 2003-7652 | 1/2003 |
| JP | 2003-152056 A | 5/2003 |
| JP | 2003-521685 | 7/2003 |
| JP | 2004537712 A | 12/2004 |
| JP | 2005-34058 | 2/2005 |
| JP | 2006-158394 | 6/2006 |
| JP | 2008-286528 | 11/2008 |
| JP | 2009-44123 | 2/2009 |
| JP | 2009260226 A | 11/2009 |
| JP | 201074135 A | 4/2010 |
| WO | WO 02/37944 A2 | 5/2002 |
| WO | WO 2008/053916 A1 | 5/2008 |

OTHER PUBLICATIONS

International Search Report dated Jun. 21, 2011 received in related Application No. PCT/JP2011/062069.
International Search Report dated Jan. 29, 2013 received in related Application No. PCT/JP2012/080106.
U.S. Office Action dated Jul. 14, 2014 issued in corresponding U.S. Appl. No. 13/686,296.
U.S. Final Office Action dated Oct. 17, 2013 issued in corresponding U.S. Appl. No. 13/686,296.
U.S. Office Action dated May 17, 2013 issued in corresponding U.S. Appl. No. 13/686,296.
Japanese Office Action dated Apr. 21, 2015 received from Application No. 2013-129934.

* cited by examiner

CELL COLLECTION APPARATUS, CELL COLLECTING SYSTEM, AND CELL COLLECTING METHOD

CROSS-REFERENCE TO RELATED APPLICATIONS

This application is a Divisional application of U.S. Ser. No. 13/686,296 filed Nov. 27, 2012, which is a continuation of PCT international application Ser. No. PCT/JP2011/062069 filed May 26, 2011 which designates the United States, incorporated herein by reference, and which claims the benefit of priority from Japanese Patent Application No. 2010-122844, filed May 28, 2010, each of which is incorporated herein by reference.

TECHNICAL FIELD

The present invention relates to a cell collection apparatus, a cell collecting system, and a cell collecting method.

BACKGROUND ART

Heretofore, the Laser Microdissection (LMD) method has been known as a technique to pick up a micro-region of about several tens microns by cutting it out from a thin tissue section for use in pathological diagnosis and the like. In the LMD method, the micro-region of the tissue section to be picked up is irradiated with UV laser, by which the micro-region is cut out from the section.

CITATION LIST

Non Patent Literature

{NPL 1}
Leica MICROSYSTEMS, "Leica LMD 7000", [online] [searched on Apr. 23, 2010], internet <URL:http://www.leica-microsystems.co.jp/Website/Products.nsf/(AL-LIDs)/9482D2B75AA53E5F49257555001FB123>

SUMMARY OF INVENTION

Technical Problem

However, in the case where a genetic test is desired to be conducted with use of a gene extracted from cells contained in a minute fragment that has been prepared by cutting out a region where specific cells such as cancer cells exist, from a section; it is not possible to extract a sufficient amount of the gene necessary for the test, because the number of cells contained in the fragment having been picked up by the LMD method is too small. Accordingly, a large number of sections have to be subject to microdissection to collect a sufficient number of cells. Therefore, large amounts of labor and time are required for conducting one genetic test.

On the other hand, it can be considered to increase the area of the fragment to be cut out, or to increase the thickness of the section to be cut out from the biological tissue. However, if the area of the fragment cut out by the LMD method is increased, it is necessary to increase the size of the laser-scannable region, or to increase the laser output so that the fragment having been cut out by laser scanning can be blown off by the pressure of laser. Therefore, the scale of the device structure has to be much enlarged and also the price of the device has to be raised. In addition, if the thickness of the section is increased, the disadvantage is that it is necessary to increase the laser output after all so as to cut out the section by laser.

The present invention addresses the above-mentioned situation. It is an object of the present invention to provide a cell collection apparatus, a cell collecting system, and a cell collecting method, capable of picking up a sufficient amount of cells for a genetic test from a section of a biological tissue with a simple structure and a simple operation.

Solution to Problem

A first aspect of the present invention is a cell collection apparatus comprising: a substrate which is provided to be dividable into a plurality of small pieces along a predetermined dividing line, and which has a flat surface to which a section of a biological tissue can be pasted; a sheet-shaped expandable member to which the substrate can be adhered in a detachable manner, and which is expandable in a direction along the surface; a expansion unit for expanding the expandable member in at least a region adhered with the substrate, in a direction along the surface; and a pickup unit for detaching and picking up the divided small pieces from the expandable member.

In the first aspect, the expandable member may have stickiness on its surface.

Moreover, in the first aspect, the substrate may comprise a plurality of separated small pieces adhered to the expandable member in mutually adjacent and aligned state.

Moreover, in the first aspect, the dividing line may be composed of a groove formed in the surface of the substrate.

Moreover, in the first aspect, the expandable member may comprise an optically transparent or semi-transparent material.

Moreover, in the first aspect, the small piece may be in a cuboid-shape having a thickness of 0.05 to 0.5 mm and side lengths of 0.05 to 5.0 mm.

Moreover, in the first aspect, the expansion unit may comprise: a fixing member for fixing a periphery of the region of the expandable member being adhered with the substrate, in a predetermined shape; and a pressing member for pressing the region of the expandable member being fixed by the fixing member, from a side of the surface opposite side to the surface adhered with the substrate.

Moreover, in the first aspect, the pickup unit may also comprise: a needle member for pushing a position of the expandable member being adhered with the small pieces, from the surface on the opposite side to the surface adhered with the small pieces.

Moreover, in the first aspect, the structure may also comprise: a holding member for holding the region of the expandable member in a expanded state.

Further, in the above-mentioned structure, the holding member may be capable of holding the surface of the expandable member on the side adhered with the substrate to be faced downward.

Moreover, the structure comprising the holding member may also comprise: a suction member which is provided to the side of the surface of the expandable member held by the holding member where the substrate is adhered, and the interior of which can be sucked to a negative pressure.

Moreover, in the first aspect, the small piece may be a magnetic particle having a diameter of 0.001 to 0.5 mm.

Moreover, in the above-mentioned structure, it is preferable that the pickup unit has a magnet which generates a magnetic force to attract the magnetic particle, in a space of an approximately same size as that of the dimension of the small piece.

Moreover, a second aspect of the present invention is a cell collecting system comprising: a cell collection apparatus according to any one of the above-mentioned structure; and an observation device for observing the section on the substrate being adhered to the expandable member.

Further, a third aspect of the present invention is a cell collecting method comprising: a pasting step for pasting a section of a biological tissue on a surface of a substrate that can be divided into a plurality of small pieces along a predetermined dividing line, while having the section bridged over the dividing line; a dividing step for dividing the substrate and the section of the biological tissue along the dividing line, by expanding the substrate pasted with the section in a direction along the surface; and a pickup step for picking up the small pieces of the section that has been divided in the dividing step.

BRIEF DESCRIPTION OF DRAWINGS

FIG. 1 shows the overall structure of the cell collecting system according to one embodiment of the present invention.
FIG. 2A is a side view of the glass substrate adhered to the sticky sheet, showing a case where the grooves are faced to the sticky sheet side.
FIG. 2B is a side view of the glass substrate adhered to the sticky sheet, showing a case where the grooves are faced to the opposite side against the sticky sheet.
FIG. 3A shows the glass substrate adhered to the sticky sheet.
FIG. 3B shows the glass substrate divided by expanding the sticky sheet.
FIG. 4 shows the structure of the expanding stage and the jig.
FIG. 5A is a diagram explaining a method how to use the expanding stage and the jig of FIG. 4, and showing a state where the sticky sheet has not been expanded yet.
FIG. 5B is a diagram explaining the method how to use the expanding stage and the jig of FIG. 4, and showing a state where the sticky sheet has been expanded.
FIG. 5C is a diagram explaining the method how to use the expanding stage and the jig of FIG. 4, and showing a state where the sticky sheet is held by the grip rings.
FIG. 6 is a flowchart explaining the procedure to pick up cells from the section with use of the cell collection apparatus and the cell collecting system of FIG. 1.
FIG. 7 shows a modified example of the substrate.
FIG. 8 shows another modified example of the substrate.
FIG. 9 shows a modified example of the cell collecting system of FIG. 1.
FIG. 10 shows another modified example of the cell collecting system of FIG. 1.
FIG. 11 is a flowchart showing a modified example the procedure to pick up cells with use of the cell collecting system of FIG. 1.
FIG. 12 is a diagram showing a modified example of the method to expand the sticky sheet with use of the outer cylinder and the inner cylinder, and showing a state where the sticky sheet is set on the outer cylinder.
FIG. 13 shows a state where the sticky sheet is being expanded by using the outer cylinder and the inner cylinder of FIG. 12.
FIG. 14 shows a state where the sticky sheet is being expanded by another method using the outer cylinder and the inner cylinder of FIG. 12.
FIG. 15A shows another modified example of the method to expand the sticky sheet before expanding the sticky sheet.
FIG. 15B shows the another modified example of the method to expand the sticky sheet after expanding the sticky sheet.
FIG. 16 shows a modified example of the grip rings.
FIG. 17 is a photograph of the section made by the Example of the present invention, showing a state before the section has been divided.
FIG. 18 is a photograph showing a state after the section of FIG. 17 has been divided.
FIG. 19 shows an example of an embodiment for detaching and picking up small pieces from the expanded sticky sheet.
FIG. 20A shows an example of an embodiment for detaching and picking up small pieces from the expanded sticky sheet by using a suction member.
FIG. 20B is an enlarged diagram showing the example of the embodiment for detaching and picking up a small piece from the expanded sticky sheet by using the suction member.
FIG. 21A shows an embodiment for picking up small pieces by a needle while tilting the expanded sticky sheet.
FIG. 21B shows an embodiment for picking up small pieces by a suction member while tilting the expanded sticky sheet.

DESCRIPTION OF EMBODIMENTS

Hereunder is a description of a cell collection apparatus 1 and a cell collecting system 100 according to one embodiment of the present invention with reference to the drawings.

Figure 1:
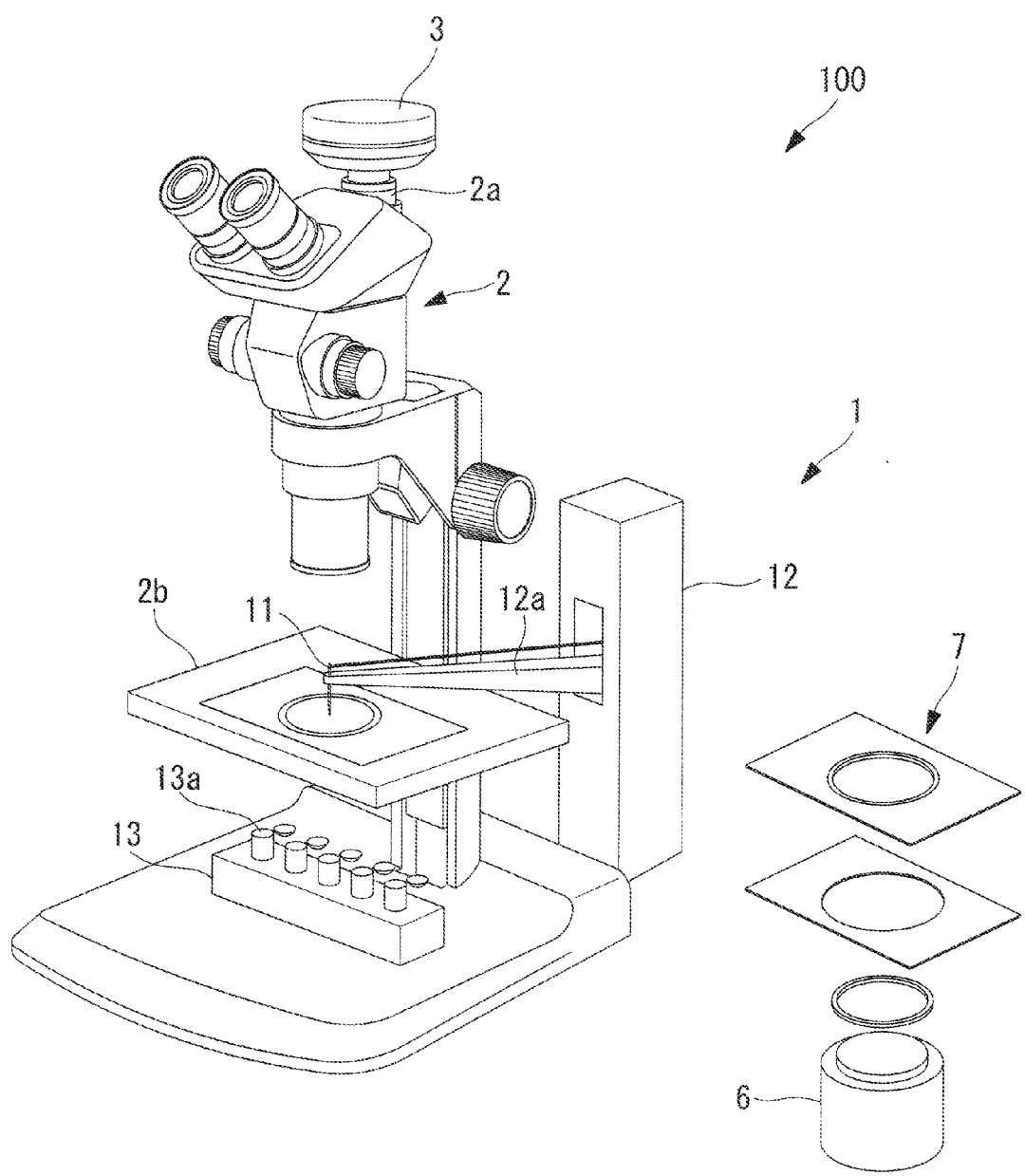
{FIG. 1}

As shown in FIG. 1, the cell collecting system 100 of this embodiment comprises an optical microscope (observation device) 2 and the cell collection apparatus 1 of this embodiment.

The optical microscope 2 is of an erecting type. The optical microscope 2 is configured such that an imaging device 3 like a CCD camera for taking an image of the field of view is connected to a camera port 2a so that the image taken by the imaging device 3 can be displayed on a monitor (not shown). The structure may also be such that the image taken by the imaging device 3 is subject to image processing with an image processing device (not shown) like an image processor and thereafter displayed on the monitor.

The cell collection apparatus 1 comprises: a glass substrate (substrate) 4 to which a section of a biological tissue can be pasted; a sticky sheet (expandable member) 5 to which the glass substrate 4 can be adhered, and which is expandable in directions along the surface; a expanding stage (expansion unit, pressing member) 6 for expanding the sticky sheet 5; a jig 7 for holding the sticky sheet 5 when the sheet 5 is being expanded by the expanding stage 6; and a pickup unit 8 for picking up small pieces 4b of the glass substrate 4 from the sticky sheet 5. By so doing, it is possible to divide the section pasted on the substrate together with the substrate along the predetermined dividing line, by expanding the expandable member with the expansion unit in a state where the substrate pasted with the section of the biological tissue is being adhered onto the expandable member. Accordingly, it is possible, by picking up small pieces adhered with section fragments containing the cells of interest, among the plurality of divided small pieces, by using the pickup unit, to pick up these cells from the section, with a simple structure and a simple operation only.

In this case, a sufficient amount of cells for a genetic test can be easily picked up only by picking up one or a several number of cells, by increasing the thickness of the section or enlarging the area of the small pieces in the planar direction so as to increase the amount of cells adhered to each small piece.

Figure 2A:
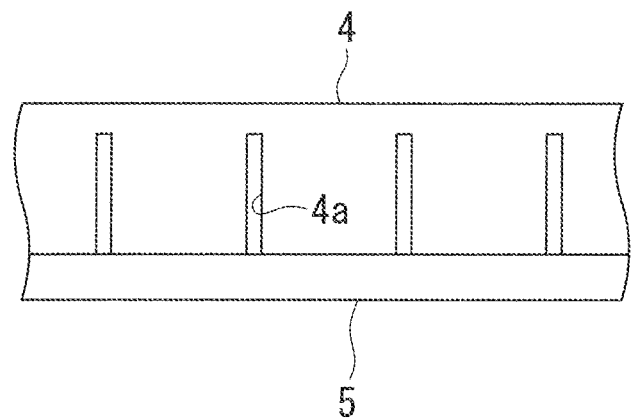
{FIG. 2A}
Figure 3A:
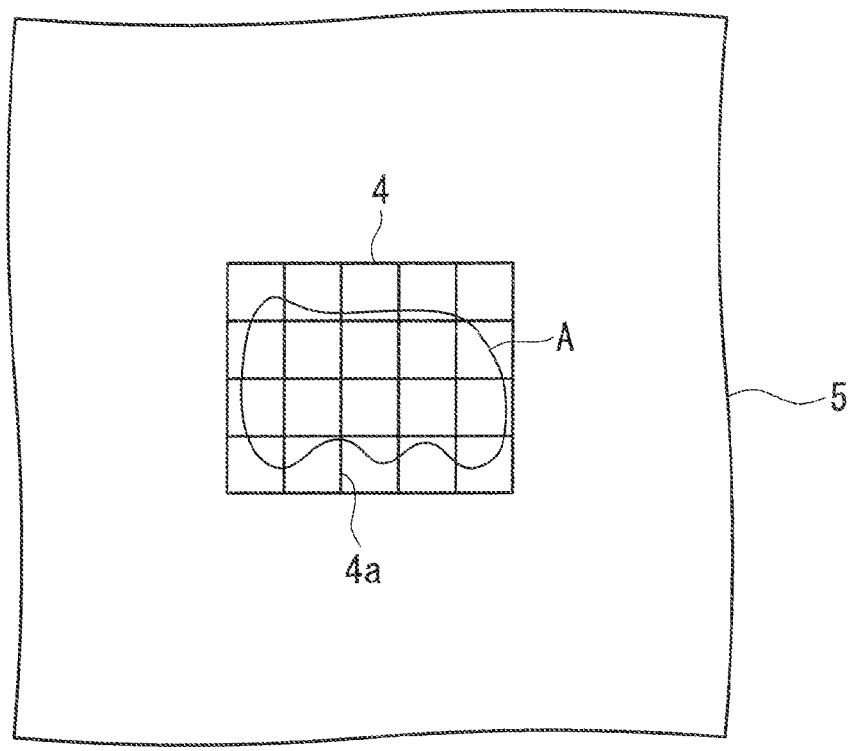
{FIG. 3A}

The glass substrate 4 is shaped like a plate having a flat surface. As shown in FIG. 2A and FIG. 3A, the surface of the glass substrate 4 is formed with grid-like grooves (dividing lines) 4a with predetermined spacing. The grooves 4a can be formed by, for example, laser processing, chemical etching, dicing, or the like. It is also possible to form them by hand work of an operator using a glass cutter or the like.

By so doing, the substrate can be easily divided along the position of the groove when the expandable member is expanded.

Preferably, the glass substrate 4 has a thickness which enables to stably support a section of a biological tissue, for example, from 0.05 to 0.5 mm. The spacing between the grooves 4a can be modified appropriately according to the size of fragments to be picked up from the section, although it is preferably from 0.05 to 5.0 mm so that a sufficient amount of cells can be contained in the picked up fragments while the fragments of a desired region can be picked up from the section with adequately precise positional accuracy. An optically transparent substrate is used for the glass substrate 4, so that the transmitted beam image of the section pasted thereon can be observed with the optical microscope 2.

By so doing, the positions of the small pieces on the expandable member can be checked at the time when observing the transmitted beam image of the expandable member with the optical microscope.

Moreover, it is also possible to apply the glass substrate 4 with silanization or such a chemical treatment on the surface so as to improve the adhesiveness between the surface and the section. Also, it is possible to apply, for example, a coating treatment for preventing adsorption of nucleic acids, proteins, and the like, according to the purpose of the test to be conducted after picking up the small pieces 4b.

Figure 3B:
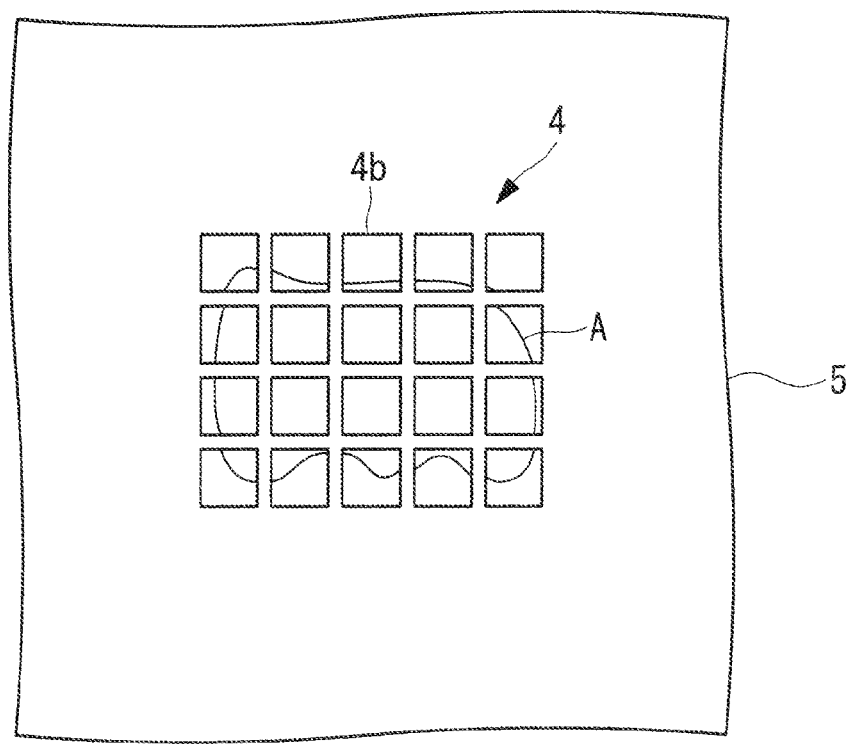
{FIG. 3B}

One surface of the sticky sheet 5 is coated with an adhesive agent to have a stickiness which enables the glass substrate 4 to be sufficiently and firmly adhered thereto, as well as enabling it to be detached therefrom by a pickup unit 8 that will be described later. By so doing, the substrate can be easily adhered onto the sticky sheet. In addition, the sticky sheet 5 is expandable in directions along the surface. When the sticky sheet 5 is expanded in a direction along the surface in a state where the glass substrate 4 is being adhered onto the sticky sheet 5, the glass substrate 4 is also extended in the direction along the surface together with the expanding of the sticky sheet 5, by which as shown in FIG. 3B the glass substrate 4 is cut along the positions of the grooves 4a and divided into a plurality of small pieces 4b. Moreover, at this time, the section A having being pasted on the surface of the glass substrate 4 is also extended in the direction along the surface, and thus cut along the grooves 4b.

The sticky sheet 5 is optically permeable or semi-permeable, by which an object arranged on the opposite side to the object lens of the optical microscope 2 can be observed across the sticky sheet 5, at the time when observing the sticky sheet 5 with the optical microscope 2. As for the sticky sheet 5, it is possible to suitably use a dicing tape for use in temporal fixation of a wafer during a dicing step in a semiconductor production process, for example.

Figure 2B:
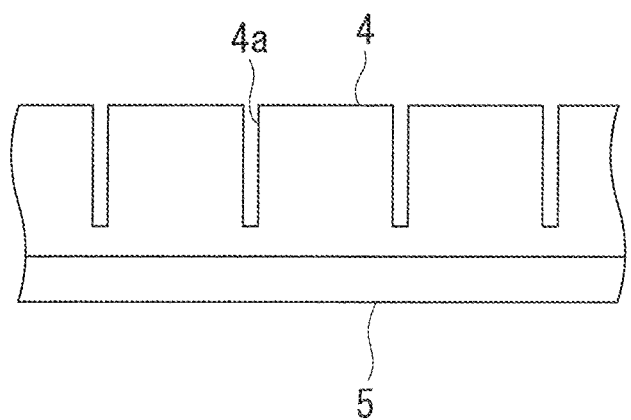
{FIG. 2B}

Note that FIG. 2A shows an example in which the glass substrate 4 is adhered to the sticky sheet 5 while the grooves 4a are facing to the sticky sheet 5 side. However, the structure may also be such that as shown in FIG. 2B the glass substrate 4 is adhered to the sticky sheet 5 while the grooves 4a are facing to the opposite side against the sticky sheet 5.

Figure 4:
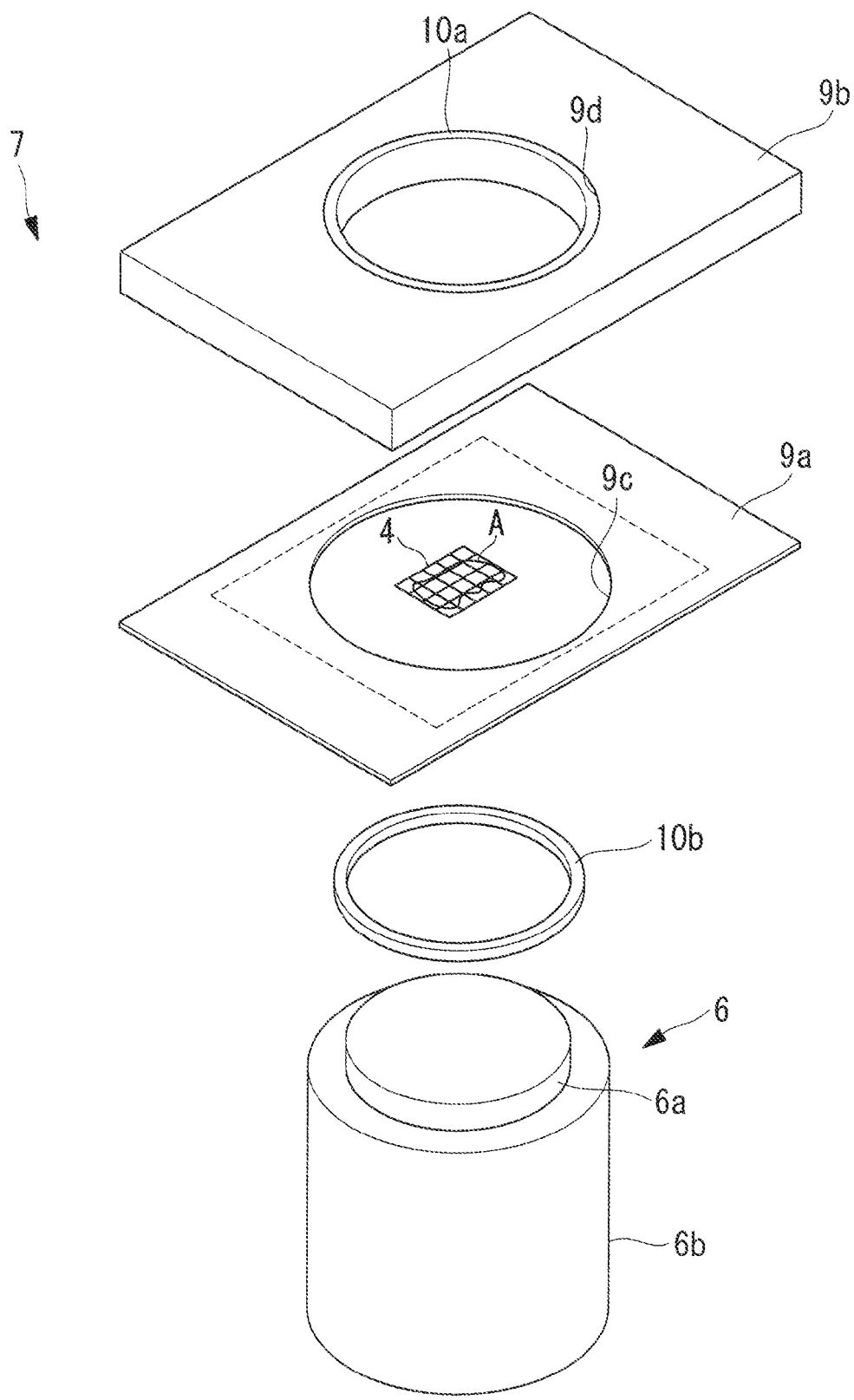
{FIG. 4}

As shown in FIG. 4, the expanding stage 6 is formed to have an approximately columnar shape with approximately parallel and flat opposite ends. In the expanding stage 6, a step is formed on the lateral surface so that the upper end portion (hereunder, referred to as the small diameter portion) 6a has a diameter smaller than that of the other portion (hereunder, referred to as the large diameter portion) 6b.

The jig 7 has a bottom frame (fixing member) 9a to which the sticky sheet 5 can be pasted in an extended state, a top frame 9b for covering the bottom frame 9a from the top, and grip rings 10a and 10b (holding member) for holding the sticky sheet 5 in a expanded state. By so doing, the expandable member can be expanded to be held in a state where the spacing between the respective small pieces is kept open. This makes it much easier to pick up the small pieces with the pickup unit. The grip rings 10a and 10b consist of an outer ring 10a and an inner ring 10b. The inner diameter of the outer ring 10a and the outer diameter of the inner ring 10b are formed to be approximately the same. In approximately the center of the bottom frame 9a and the top frame 9b, windows 9c and 9d passing through in the plate thickness direction are respectively formed. The outer ring 10a is fit inside the window 9d of the top frame 9b, along the inner circumferential surface thereof. The window 9c of the bottom frame 9a has the same or larger diameter than the outer diameter of the small diameter portion 6a.

Figure 5A:
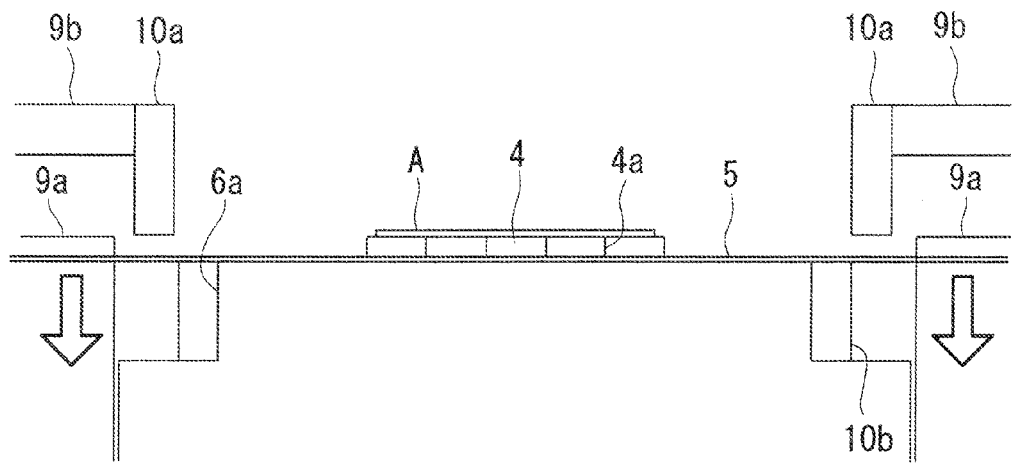
{FIG. 5A}
Figure 5B:
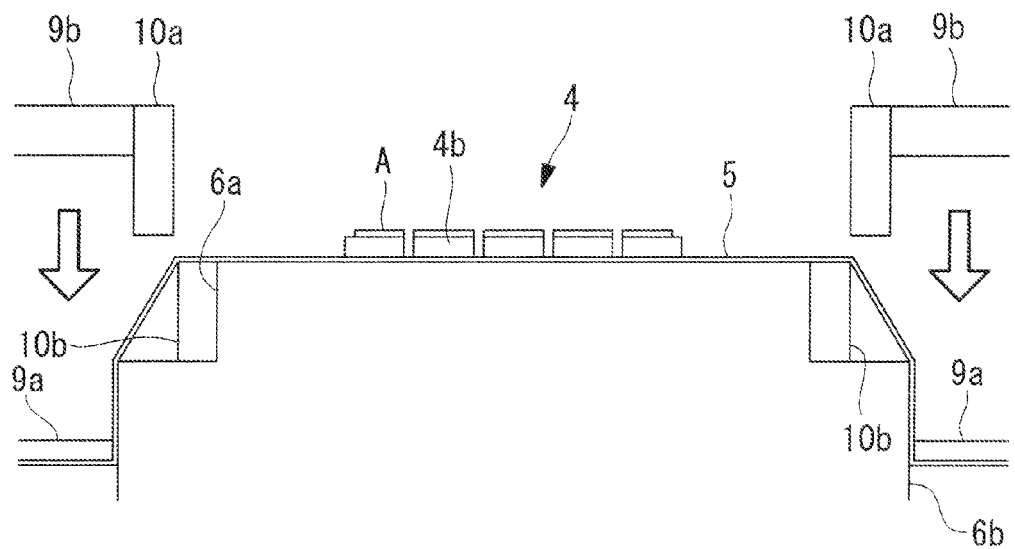
{FIG. 5B}

The jig 7 is used in the following manner. Firstly, the inner ring 10b is fit along the outer circumference of the small diameter portion 6a. Then, the sticky sheet 5 adhered with the glass substrate 4 is adhered to the bottom surface of the bottom frame 9a in a state where the glass substrate 4 is arranged in a position of the window 9c and the surface on the side adhered with the glass substrate 4 is facing upward. By so doing, as shown in FIG. 5A, the periphery around the region adhered with the glass substrate 4 of the sticky sheet 5 is fixed in a predetermined shape. Next, the bottom frame 9a is pressed to move downward in a state where a portion of the sticky sheet 5 corresponding to the window 9c is being pressed against the top surface of the expanding stage 6. By so doing, as shown in FIG. 5B, the portion of the sticky sheet 5 corresponding to the window 9c is expanded by being pressed from the expanding stage 6, and the glass substrate 4 is divided into a plurality of small pieces 4b together with the expanding of the sticky sheet 5.

Figure 5C:
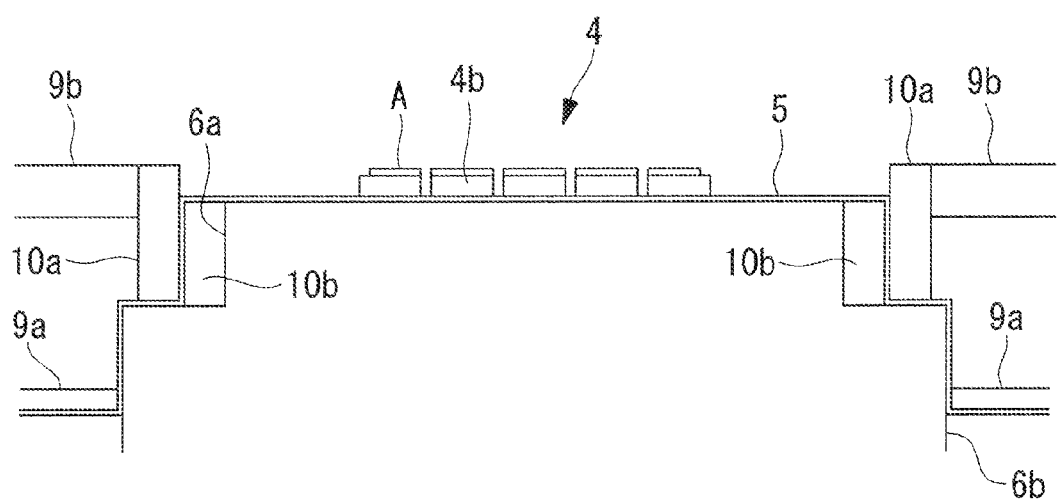
{FIG. 5C}

Next, as shown in FIG. 5C, the outer ring 10a and the inner ring 10b are fit to each other by covering the top frame 9b over the bottom frame 9a in a state where the sticky sheet 5 is being expanded. By so doing, the portion of the sticky sheet 5 corresponding to the window 9c is held in a expanded state by the grip rings 10a and 10b.

It is also possible to put a mark, for example, a scale mark, on the sticky sheet 5 for the purpose of understanding the degree of how much the sticky sheet 5 is expanded when the sticky sheet 5 is being expanded in this manner.

The pickup unit 8 comprises a pickup needle 11 and a manipulator 12 for operating the pickup needle 11. The tip of the pickup needle 11 has a diameter approximately the same as or smaller than the size of each small piece 4b. The manipulator 12 holds the pickup needle 11 at the distal end of the arm 12a. The manipulator 12 is designed to move the arm 12a in three dimensional directions by the operation of the operator.

By so doing, only specific small pieces can be easily detached and picked up, among the plurality of small pieces, from the expandable member.

Figure 6:
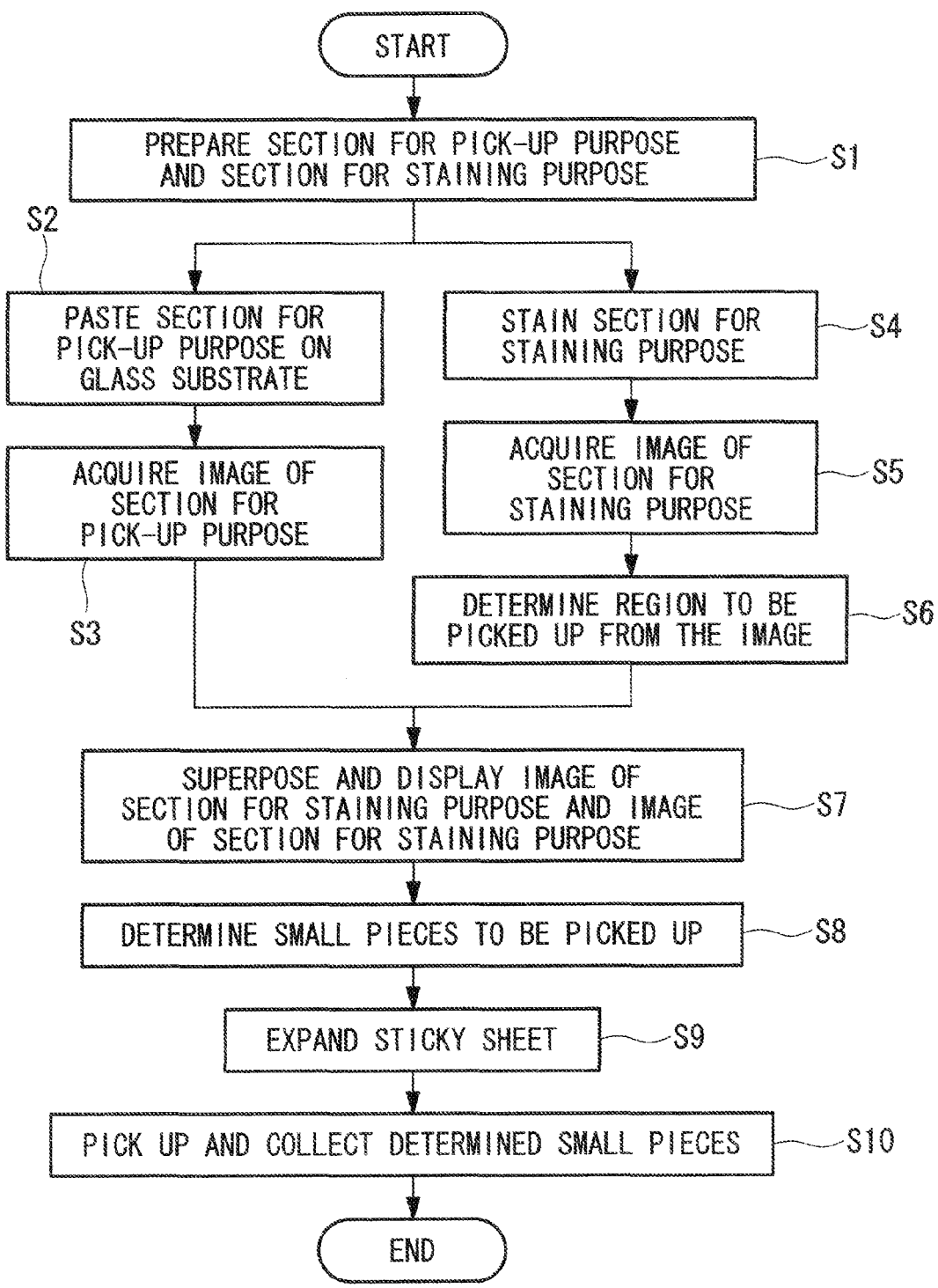
{FIG. 6}

Hereunder is a description of the method to pick up fragments containing cells of interest from a section of a biological tissue by using the thus configured cell collection apparatus 1 and cell collecting system 100, with reference to FIG. 6.

In order to pick up the target cells from a section of a biological tissue by using the cell collection apparatus 1 and the cell collecting system 100 according to this embodiment: firstly, the section for pick-up purpose (section) is cut out from the biological tissue (Step S1); and the thus cut out section for pick-up purpose is pasted on the glass substrate 4 (Step S2, Pasting Step). Then, the analyte section image is acquired by observing the section for pick-up purpose with the optical microscope 2 (Step S3).

The section for pick-up purpose is cut out by, for example, freeze sectioning or paraffin sectioning. The thickness of the section for pick-up purpose may be thicker than the thickness of a usual section for use as a pathological sample or the like (about several to ten micrometers), although it depends on the purpose of the application of the picked up cells. For example, the section for pick-up purpose can be cut out to have a thickness of about 50 μm. If the size of the thus cut out section for pick-up purpose is smaller than the spacing between the grooves 4a of the glass substrate 4, the section for pick-up purpose is pasted on the glass substrate 4 so that the section for pick-up purpose can be bridged over the groove 4a.

Moreover, differently from the section for pick-up purpose, a section for staining purpose is cut to have a thickness of about several to ten micrometers from the place adjacent to the place where the section for pick-up purpose of the biological tissue has been cut out. The thus cut out section for staining purpose is pasted on a slide glass and then stained with, for example, a dye for pathological diagnosis (Step S4). Then, the stained-section image is acquired by observing the stained section for staining purpose with the optical microscope 2 (Step S5). In the acquired stained-section image, the region to be picked up where the cells of interest exist, for example, a region infiltrated by cancer cells, is determined (Step S6).

Next, the acquired analyte section image and the stained-section image are superposed and displayed so that the sections in the respective images can exactly overlap each other (Step S7), and the positions of the small pieces 4b corresponding to the determined region to be picked up in the section for staining purpose, for example, the column numbers and the row numbers of the small pieces 4b, are recorded (Step S8).

Next, the glass substrate 4 is adhered to the sticky sheet 5. It is also possible to paste the cut out section for pick-up purpose, onto the glass substrate 4 that has been previously adhered to the sticky sheet 5. Next, the sticky sheet 5 is expanded by using the expanding stage 6 and the jig 7, to thereby divide the glass substrate 4 (Step S9, Dividing Step). At this time, the section for pick-up purpose pasted on the glass substrate 4 is also extended together with the glass substrate 4 in the planar direction, by which the section is divided into fragments along the positions of the grooves 4a.

Next, the sticky sheet 5 is held in a expanded state by the grip rings 10a and 10b, and the sticky sheet 5 is set on the specimen stage 2b so that the surface on the side adhered with the glass substrate 4 is faced downward. At this time, it is either possible to set the sticky sheet 5 on the specimen stage 2b in a state detached from the bottom frame 9a, or to set the sticky sheet 5 on the specimen stage 2b together with the bottom frame 9a.

Next, while observing the small pieces 4b in the recorded positions with the optical microscope 2, the manipulator 12 is operated within the field of view thereof to arrange the pickup needle 11 on the back of a small piece 4b to be picked up. The back face of the small piece 4b to be picked up is pushed with the pickup needle 11 to thereby detach and drop the small piece 4b from the sticky sheet 5 (Step S10, Pickup Step). At this time, it is also possible to arrange a tube rack 13 under the specimen stage 2b so that collection tubes 13a can be previously arranged in the positions where the small pieces 4b would drop.

By so doing, it is possible to detach the small pieces in a state where the sticky sheet is held in a state where the substrate is facing downward, by using the grip rings. This makes it possible to easily collect the small pieces by letting them drop by their own weights.

Throughout the above-mentioned procedure, fragments of the region where the cells of interest exist can be picked up from the section for pick-up purpose, together with the small pieces 4b. The picked up cells are used in, for example, a genetic test or the like.

In other words, the selection of small pieces to be picked up and the pickup of the selected small pieces can be more easily and accurately conducted, through observation of the section pasted on the substrate, the small pieces formed after dividing the substrate, and the like, with the optical microscope.

In this way, according to this embodiment, the advantage is that the region where the cells of interest exist can be selectively picked up from the section with a simple structure and a simple operation only. In addition, since there is no need of an expensive structure such as a UV laser light source, another advantage is that the production cost can be kept low. Moreover, unlike the LMD, the section is mechanically cut. Thus, a section having a relatively thick thickness can be easily cut, and also the sizes of the small pieces 4b can be easily enlarged only by adjusting the spacing between the grooves 4a. Accordingly, the operation that has so far required a large amount of labor because fragments have to be picked up from a plurality of sections so as to collect a sufficient number of cells, can be sufficed only by picking up one or a small number of small pieces 4b. Thus, the advantage is that the labor and the time required for the operation can be remarkably reduced.

In the above-mentioned embodiment, the glass substrate 4 formed with the grid-like grooves 4a is used as the substrate for pasting the section. However, instead of this, it is also possible to use a glass substrate 4 comprising glass-made small pieces 4b aligned in the planar direction.

Figure 7:
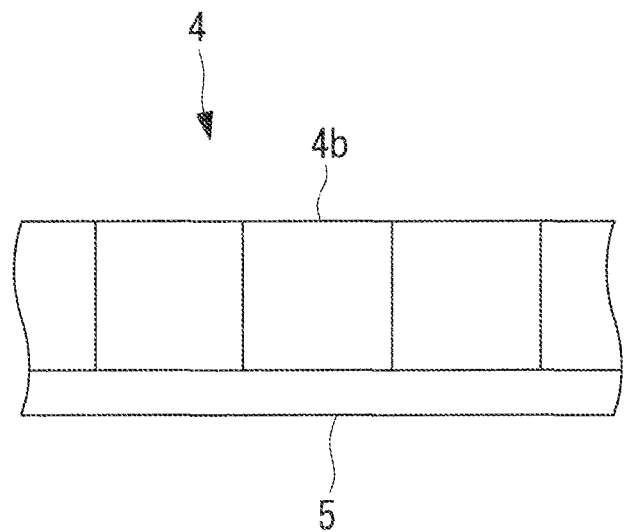
{FIG. 7}

In this case, in order to keep the shape of the glass substrate 4, the glass-made small pieces 4b are previously adhered onto the sticky sheet 5 in an aligned state as shown in FIG. 7. By so doing, the glass substrate 4 can be more easily and reliably divided along the border (dividing lines) between the small pieces 4b when the sticky sheet 5 is expanded.

The following method can be adopted as an example to produce the aligned state of the previously divided small pieces on the sticky sheet 5.

The glass substrate 4 is adhered on the sticky sheet 5, and the glass substrate 4 is scratched by a glass cutter. Then, the glass substrate 4 is cracked along the position of the scratch by hand. By so doing, the aligned state of the small pieces 4b on the sticky sheet 5 as shown in FIG. 7 can be easily produced. At this time, it is preferable to carry out this procedure while protecting the surface of the glass substrate 4 with a film or the like so as to avoid contamination of the glass substrate 4.

In addition, the structure of the substrate employed in the above-mentioned embodiment is only an example, and the present invention is not to be limited to this structure.

Figure 8:
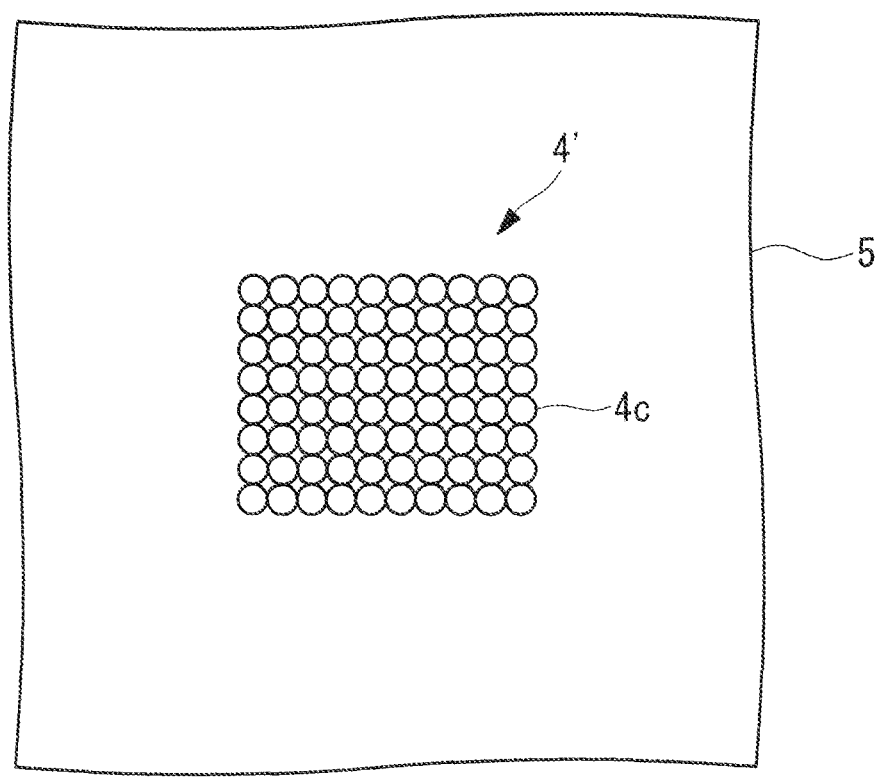
{FIG. 8}

For example, the material of the substrate may be not only a glass but also a resin or the like. Regarding the shape of the small piece 4b, any shape may be adopted as long as the small pieces 4b can be densely aligned on the surface of the sticky sheet 5. For example, a regular hexagonal shape or a triangular shape may be adopted. Moreover, as shown in FIG. 8, it is also possible to configure the substrate 4' by using globular glass beads or resin beads 4c as the small pieces and aligning them on the sticky sheet 5, preferably in a single layer.

In addition, a material having a magnetic property may also be used as the substrate. For example, it is possible to densely align magnetic particles having a diameter of 1 to 500 µm on the surface of the sticky sheet 5, and to use a metal plate of such as a stainless-steel as the substrate. By so doing, a treatment can be made more efficient, for example, by isolating the collected small pieces from a solution with use of the magnetic force when the small pieces are treated in the solution. If a material such as a metal which does not allow the transmission of visible light is used as the substrate, the small pieces 4b, even though these are small, can be clearly observed by eyes at the time when observing the transmitted beam image of the sticky sheet 5 with the optical microscope.

In this case, a magnet can be used as the pickup unit 8. For example, a magnet having approximately the same size as that of the magnetic particle is provided at the tip of the pickup needle 11. Then, the tip of the pickup needle 11 is brought closer to a magnetic particle from the opposite side against the sticky sheet 5, by which a desired magnetic particle can be held on the tip of the pickup needle 11 and picked up from the sticky sheet 5 by the magnetic force.

Moreover, in the above-mentioned embodiment, the employed structure is such that the optical microscope 2 of an erecting type is used and the expanding stage 6 is provided separately from the optical microscope 2. However, the structure of the cell collecting system 100 is not to be limited to this. For example, an inverted type can be adopted as the optical microscope 2, and the expanding stage 6 can be installed in the optical microscope 2.

Figure 9:
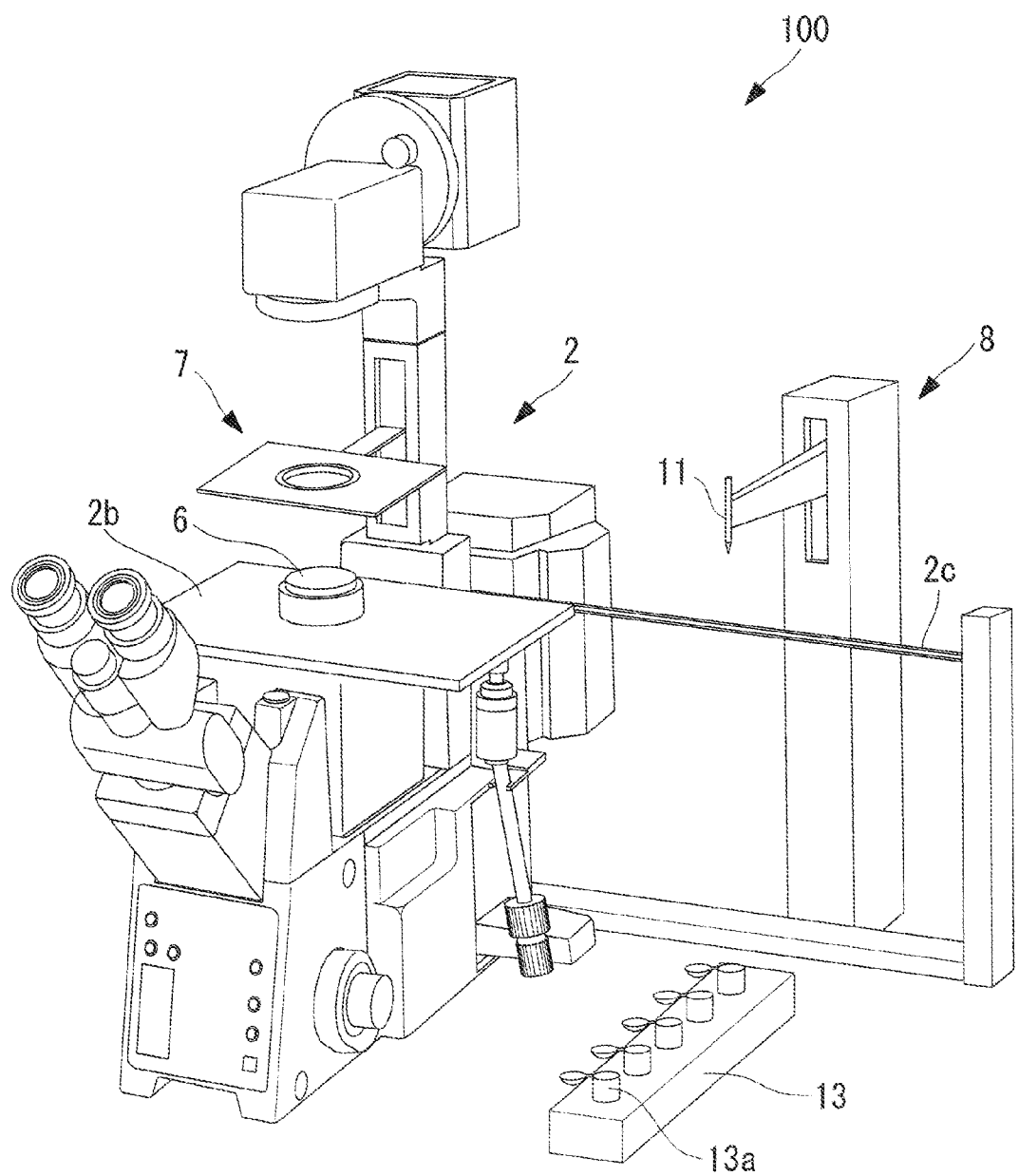
{FIG. 9}

FIG. 9 shows an example of the structure in which the expanding stage 6 and the jig 7 are provided to an inverted-type optical microscope 2. The specimen stage 2b is provided slidably in the horizontal direction along a guide rail 2c bridged between the observation position of the optical microscope 2 and a position out of the main body of the optical microscope 2. In such a structure, the sticky sheet 5 is expanded on the expanding stage 6 by moving the jig 7 downward in a state where the specimen stage is arranged in the observation position. Thereafter, the specimen stage 2b is slid and the small pieces 4b are picked up by using the pickup unit 8 having been provided separately from the optical microscope 2.

Figure 10:
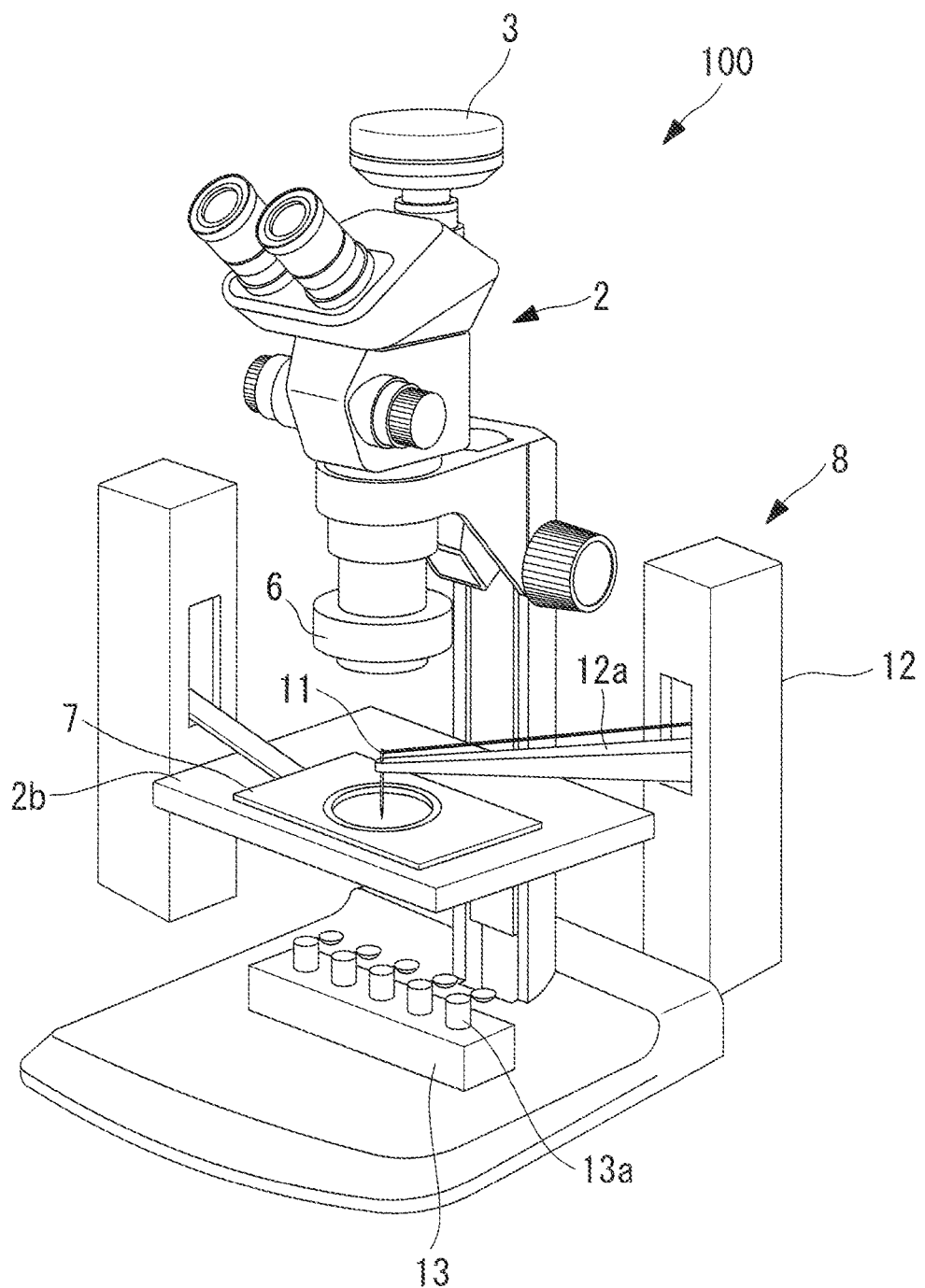
{FIG. 10}

FIG. 10 shows an example of the structure in which the expanding stage 6, the jig 7, and the pickup unit 8 are provided to an inverted-type optical microscope 2. The expanding stage 6 is provided above the specimen stage 2b so that the stage can be moved integrally with the object lens in the vertical direction, and the expanding stage 6 is designed to be pushed against the sticky sheet 5 held on the specimen stage 2b by the jig 7, from the above. In this structure, a series of operations from the expanding of the sticky sheet 5 to the pickup of the small pieces 4b can be done on the specimen stage 2b.

Moreover, in the above-mentioned embodiment, the small pieces 4b to be picked up are determined by making a comparison between the analyte section image of the section for pick-up purpose and the stained-section image of the section for staining purpose. However, instead of this, it is also possible to determine the small pieces 4b to be picked up from the image of the section for pick-up purpose.

Figure 11:
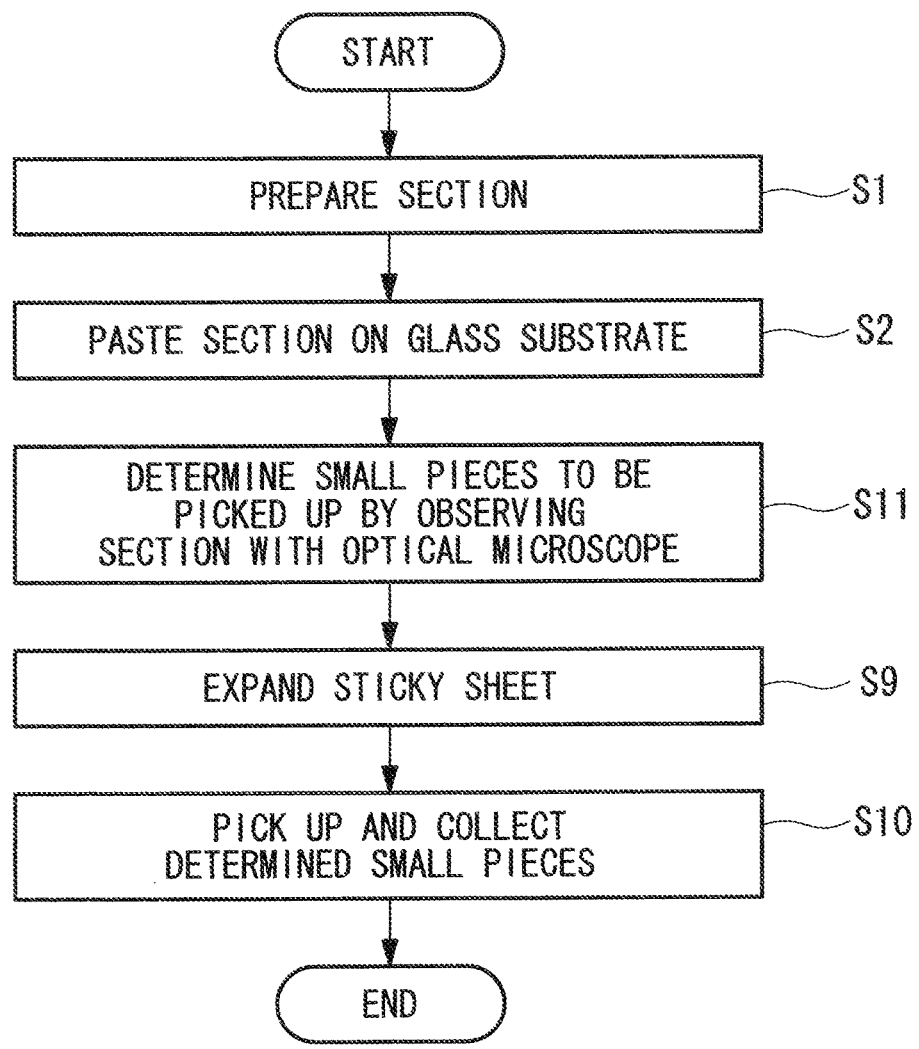
{FIG. 11}

In the case where a section for pick-up purpose has a relatively thick thickness, cells are overlapped in the thickness direction. This makes it difficult to accurately recognize the shape of each cell, the distribution of cells, and the like, from the image, even though the image is stained. However, even from such a stained-section image or an unstained-section image of the section, in the case where the determination of the region to be picked up is possible based on a rough shape of the tissue or on the distribution of cells, for example as shown in FIG. 11, the small pieces 4b to be picked up can be selected using the same image while observing the section for pick-up purpose with the optical microscope 2 (Step S11). Thereafter, the sticky sheet 5 can be expanded (Step S9) and the small pieces 4b can be picked up (Step S10). By so doing, the procedure can be much more simplified as required.

Moreover, in the above-mentioned embodiment, the approximately columnar expanding stage 6 is used to expand the sticky sheet 5. However, the unit to expand the sticky sheet 5 is not to be limited to this.

For example, instead of the expanding stage 6, an outer cylinder 14a and an inner cylinder 14b that can be accommodated in the outer cylinder 14a can be adopted.

Figure 12:
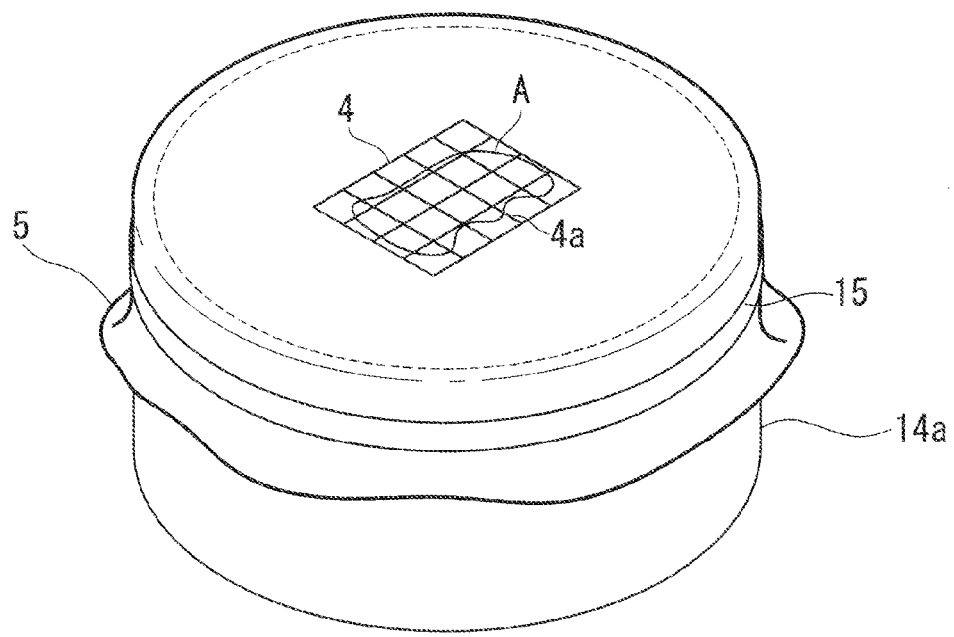
{FIG. 12}
Figure 13:
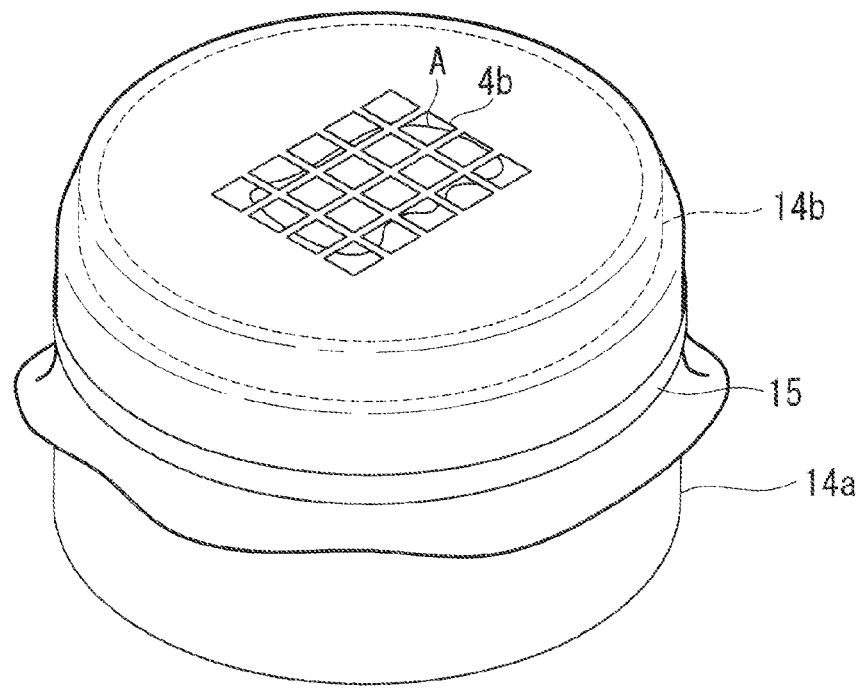
{FIG. 13}
Figure 14:
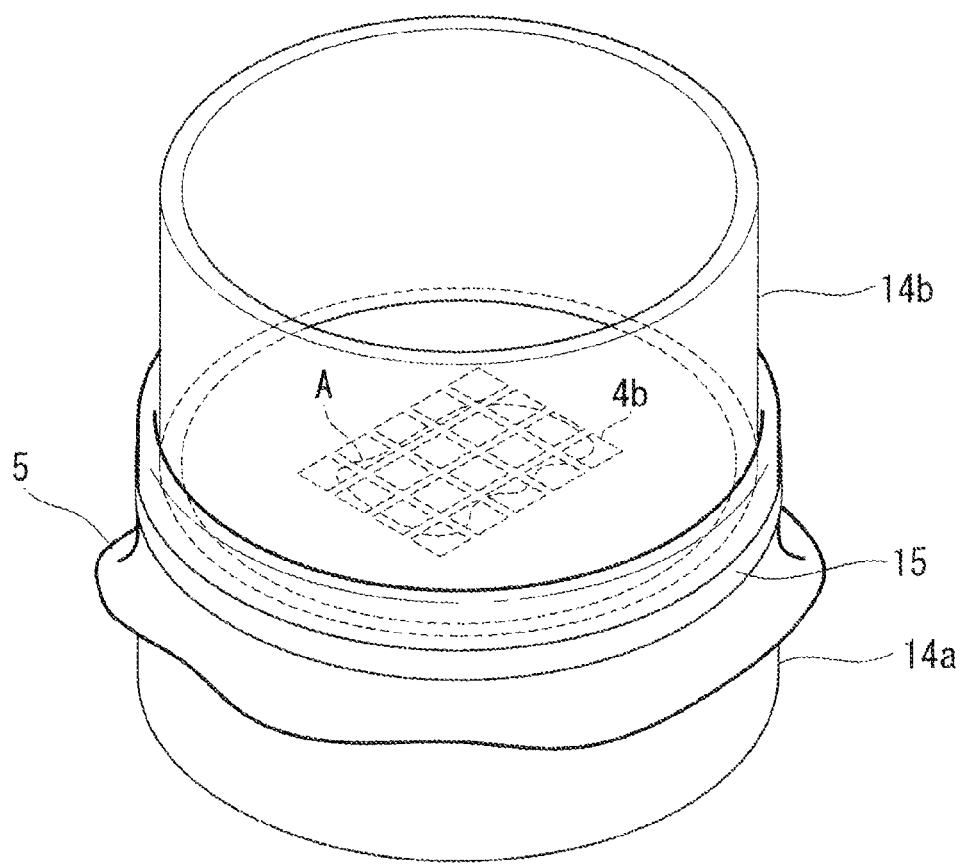
{FIG. 14}

In this case, as shown in FIG. 12, the sticky sheet 5 is covered over the top surface of the outer cylinder 14a and fixed to the lateral surface of the outer cylinder 14a. The symbol 15 denotes a fixing member for fixing the sticky sheet 5 to the lateral surface of the outer cylinder 14a. Next, as shown in FIG. 13 the inner cylinder 14b is protruded relatively from the inside of the outer cylinder 14a, or as shown in FIG. 14 the inner cylinder 14b is pushed relatively from the outside of the outer cylinder 14a into the inside of the outer cylinder 14a. By so doing, the sticky sheet 5 can be expanded approximately evenly in every direction.

Figure 15A:
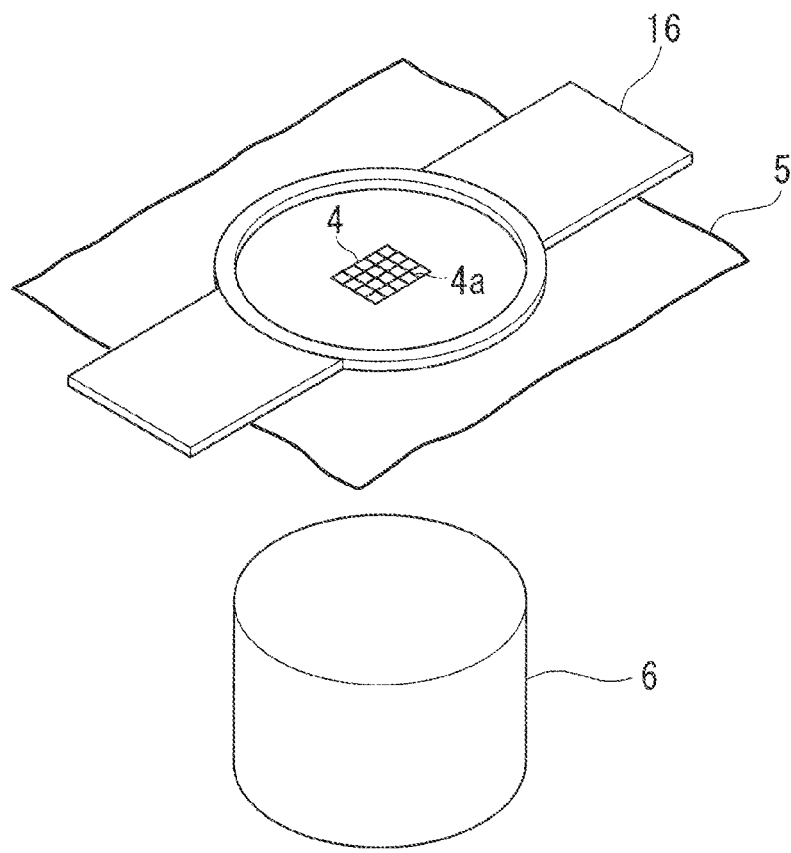
{FIG. 15A}
Figure 15B:
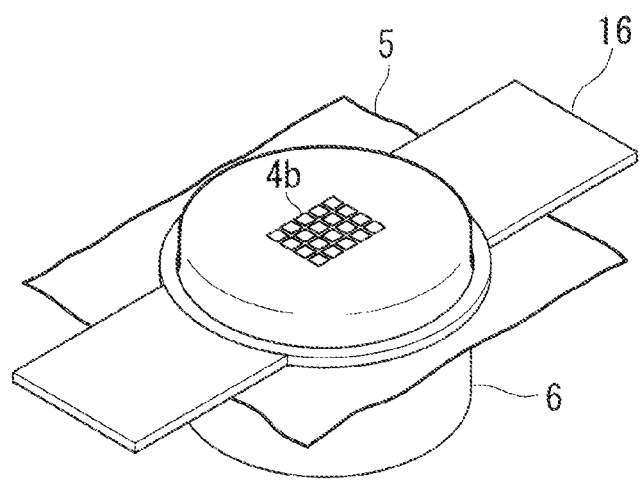
{FIG. 15B}

In addition, the structure may also be such that as shown in FIG. 15A the sticky sheet 5 is held in a certain shape by the holder 16 in a position where the region adhered with the glass substrate 4 can be seen, and as shown in FIG. 15B the sticky sheet 5 is expanded by pressing the region adhered with the glass substrate 4 against the expanding stage 6.

Figure 16:
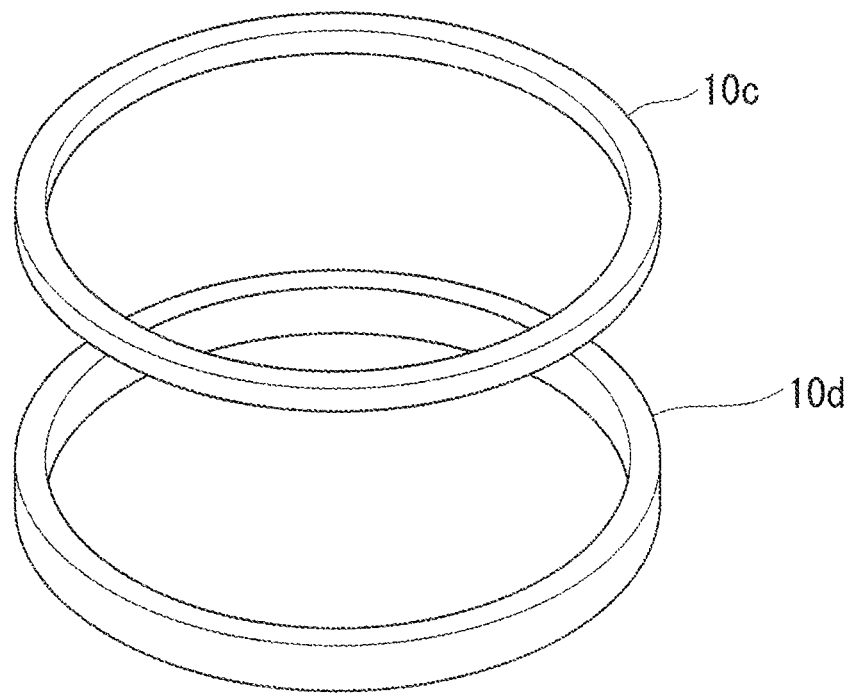
{FIG. 16}

Moreover, as for the grip rings, it is also possible to adopt rings that can be held in a mutually and tightly attached state by a magnetic force. For example, as shown in FIG. 16, grip rings 10c and 10d can be composed of a top ring 10c made from a magnet and an bottom ring 10d made from a metal such as a stainless-steel having the same diameters, so that the both rings 10c and 10d can be tightly attached to each other by a magnetic force while sandwiching the sticky sheet 5 in a expanded state between the top ring 10c and the bottom ring 10d. By so doing, the sticky sheet 5 can be held in a expanded state. The both rings 10c and 10d may also be composed of magnets which generate attracting forces each other.

Moreover, in the above-mentioned embodiment, a small piece 4b is detached and collected from the sticky sheet 5 by pushing the small piece 4b from the back with the pickup needle 11. However, instead of this, it is also possible to use a suction member the interior of which can be sucked to a negative pressure. By so doing, a small piece 4b to be picked up can be detached from the sticky sheet 5 and collected into the suction member by bringing the suction member closer to the small piece 4b from the opposite side against the sticky sheet 5.

Moreover, a substance that loses the stickiness by UV irradiation can also be used as the sticky sheet 5.

In this case, for example, a UV light source is equipped in the optical microscope 2. Also, UV light radiated from the UV light source is irradiated locally to the position of a small piece 4b to be picked up through the object lens, by which the small piece 4b can be easily detached and collected from the sticky sheet 5. Besides, a similar effect can also be achieved by guiding UV light through an optical fiber and locally irradiating the light toward the position of the small piece 4b to be picked up while orienting the fiber end thereto.

<Embodiment for Picking Up Small Pieces by Suction>

It is also possible to pick up an optional small piece from the sticky sheet by using a tubular suction member in which a hole having a size not allowing each small piece to pass through, is made at the tip. The interior of the suction member can be set to a negative pressure as required, by which the small piece can be adhered at the tip, and then transferred and picked up from the top of the sticky sheet. It is also possible to adopt a form in which a plurality of such tubular suction members are bundled, or to make a plurality of holes having sizes not allowing each small piece to pass through, in an arrangement corresponding to the spacing between the small pieces in a expanded state, at the tip of the tubular suction member. By using such a member, a plurality of small pieces can be picked up at the same time.

In addition, it is also possible to make the size of the hole in the tubular suction member larger than each small piece so that small pieces can be collected into the tube by sucking.

Furthermore, it is also possible to set a suction member made from a conductive material. By so doing, the small pieces can be more easily handled because electricity can be removed from the small pieces even though they have been electrified.

<Embodiment for Picking Up Small Pieces after Detachment of all or a Part of Small Pieces from the Expanded Sticky Sheet>

Figure 19:
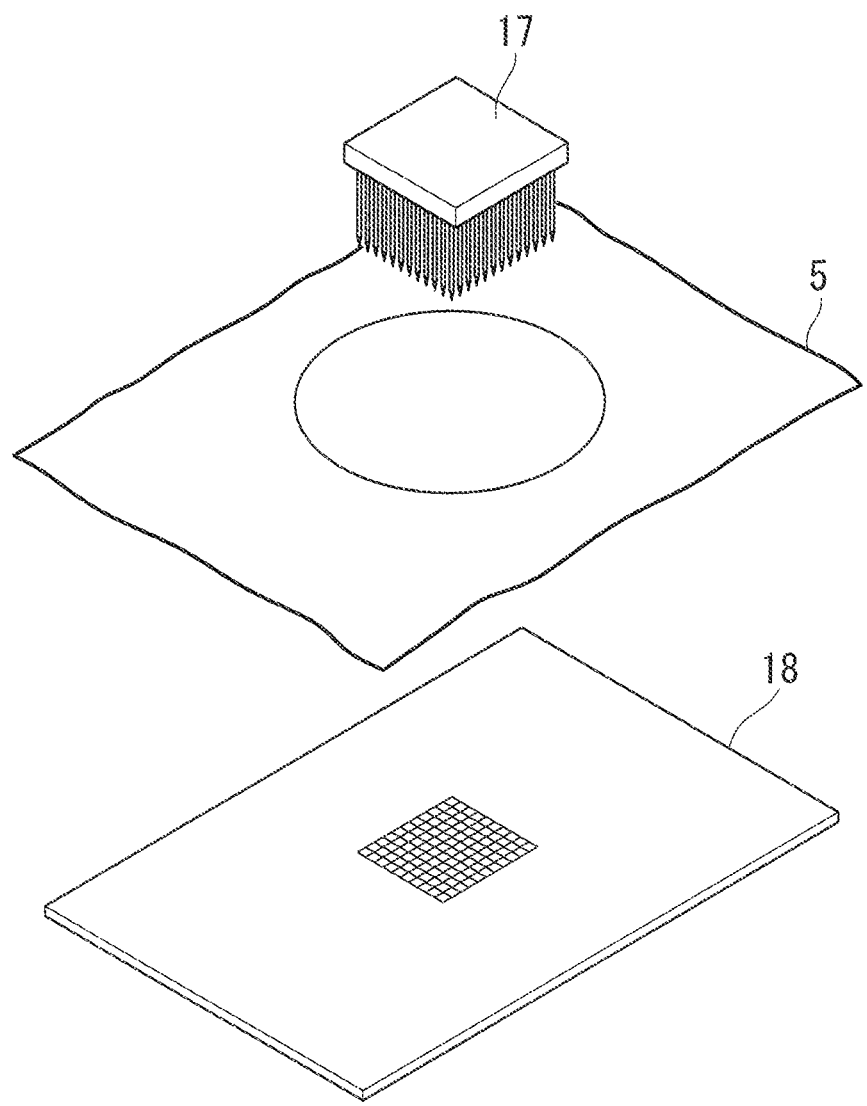
{FIG. 19}
Figure 20A:
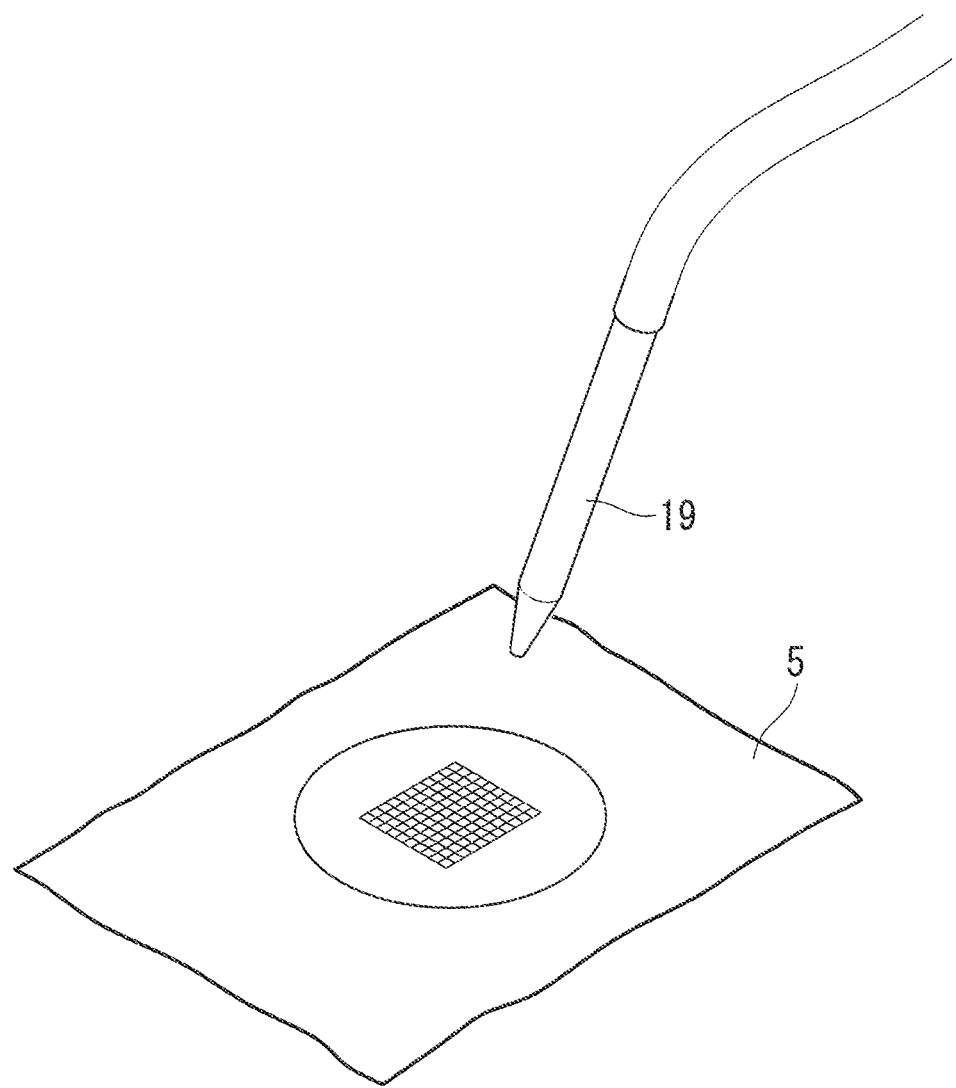
{FIG. 20A}
Figure 20B:
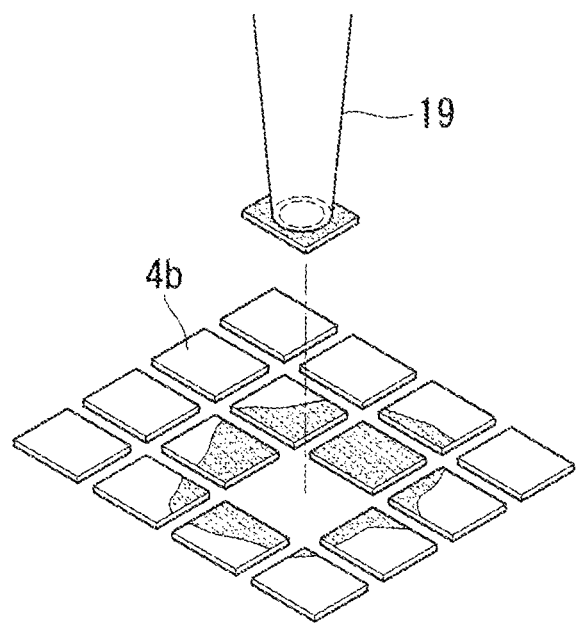
{FIG. 20B}

If a UV-sensitive adhesive is used for the sticky sheet, the stickiness can be weakened by UV irradiation. It is possible to detach all or optional small pieces onto the flat plate 18 by a needle assembly member 17 as shown in FIG. 19 in a state where the stickiness has been weakened in such a sticky sheet, and to pick up necessary small pieces from the group of the detached small pieces on the flat plate 18. Regarding the method for picking up, it is possible to pick up by holding each piece with a pair of tweezers, or to pick up by sucking each piece with the above-mentioned tubular suction member 19 as shown in FIG. 20A or FIG. 20B.

<Embodiment for Picking Up Small Pieces with a Needle or a Suction Member while Tilting the Expanded Sticky Sheet>

Figure 21A:
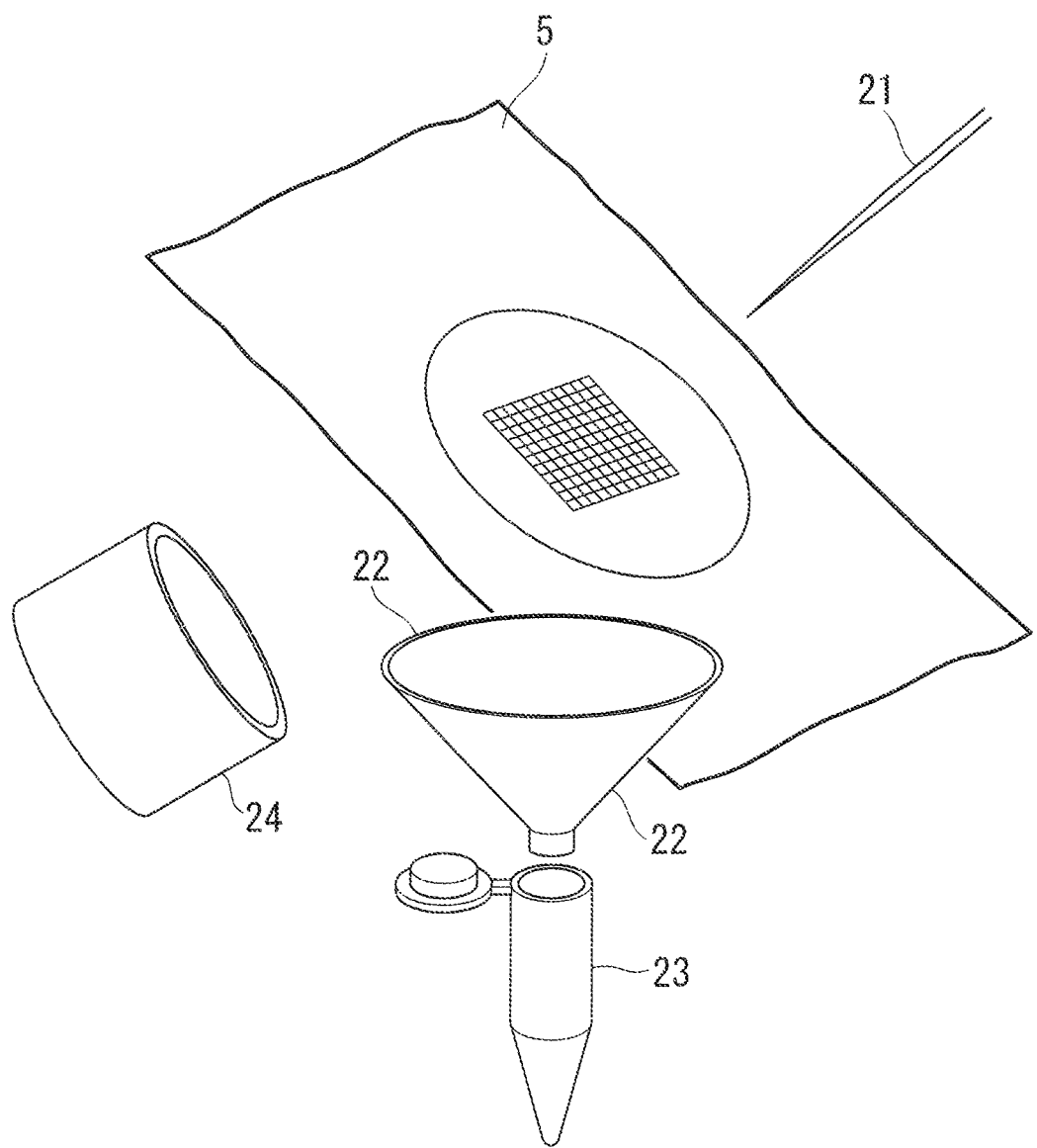
{FIG. 21A}
Figure 21B:
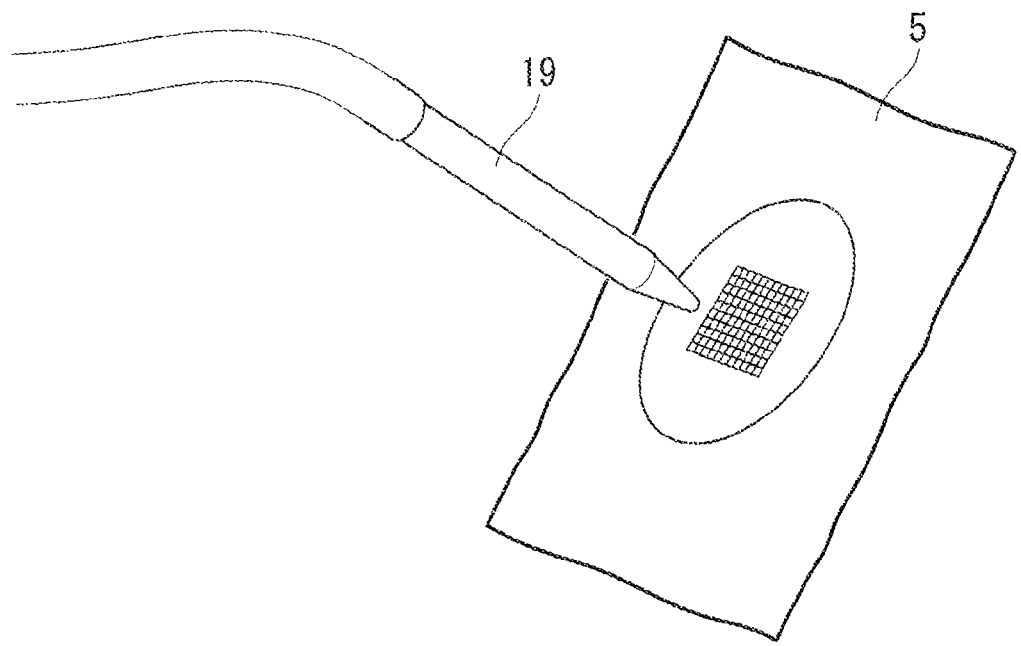
{FIG. 21B}

It is also possible to pick up small pieces not by orienting the expanded sticky sheet vertically downward but by tilting it relative to the vertical line to drop them. In this case, it is easier to arrange an observation unit 24 to observe the small pieces and a container 23 for collecting the dropped small pieces, as compared to the case where the sticky sheet is set horizontal. Regarding the method for picking up, as shown in FIG. 21A, a funnel-shaped guide member 22 can be used to pick up the small pieces having been dropped by pushing from the back of the expanded sticky sheet 5 with a needle 21. Or, they can be picked up by sucking with the above-mentioned tubular suction member 19 as shown in FIG. 21B.

<Embodiment for Collecting Small Pieces by Arranging a Funnel-shaped Member Above a Container>

It is also possible to arrange a sufficiently large funnel-shaped member above the collection container. By so doing, small pieces can be easily picked up without dropping out from the collection container even though its opening is small.

EXAMPLE

Next is a description of Example of the above-mentioned embodiment.

In this Example, the following experiment was conducted so as to confirm that the cell collection apparatus was capable of dividing a section of a biological tissue.

A pig colon was used as the biological tissue. A section having four side lengths of about 10 mm and a thickness of 50 µm was cut out from the biological tissue by freeze sectioning. The cut out section was pasted on two cover glasses, which had been aligned to be adjacent to each other at the corners and pasted on a dicing sheet (expandable member), so that the section was bridged over the border (dividing line) between these cover glasses. Thereafter, the section was dried by air. The cover glass used herein had respective side lengths of 18 mm and a thickness of 0.13 to 0.17 mm.

Next, the dicing tape was pasted on the top frame having a circular window formed through an approximate center thereof, so that the section was arranged in an approximate center of the window. Next, the surface pasted with the cover glasses was faced upward. In a state where the columnar stage was arranged in the window, the top frame was pushed down while being kept approximately horizontal, by which the portion of the dicing tape arranged within the window was expanded in the planar direction. By so doing, these two cover glasses was separated from each other, and the section pasted on the cover glasses was divided into two fragments along the border between the cover glasses. The photographs of the section before and after dividing the section in this way are shown in FIG. 17 and FIG. 18.

Figure 17:
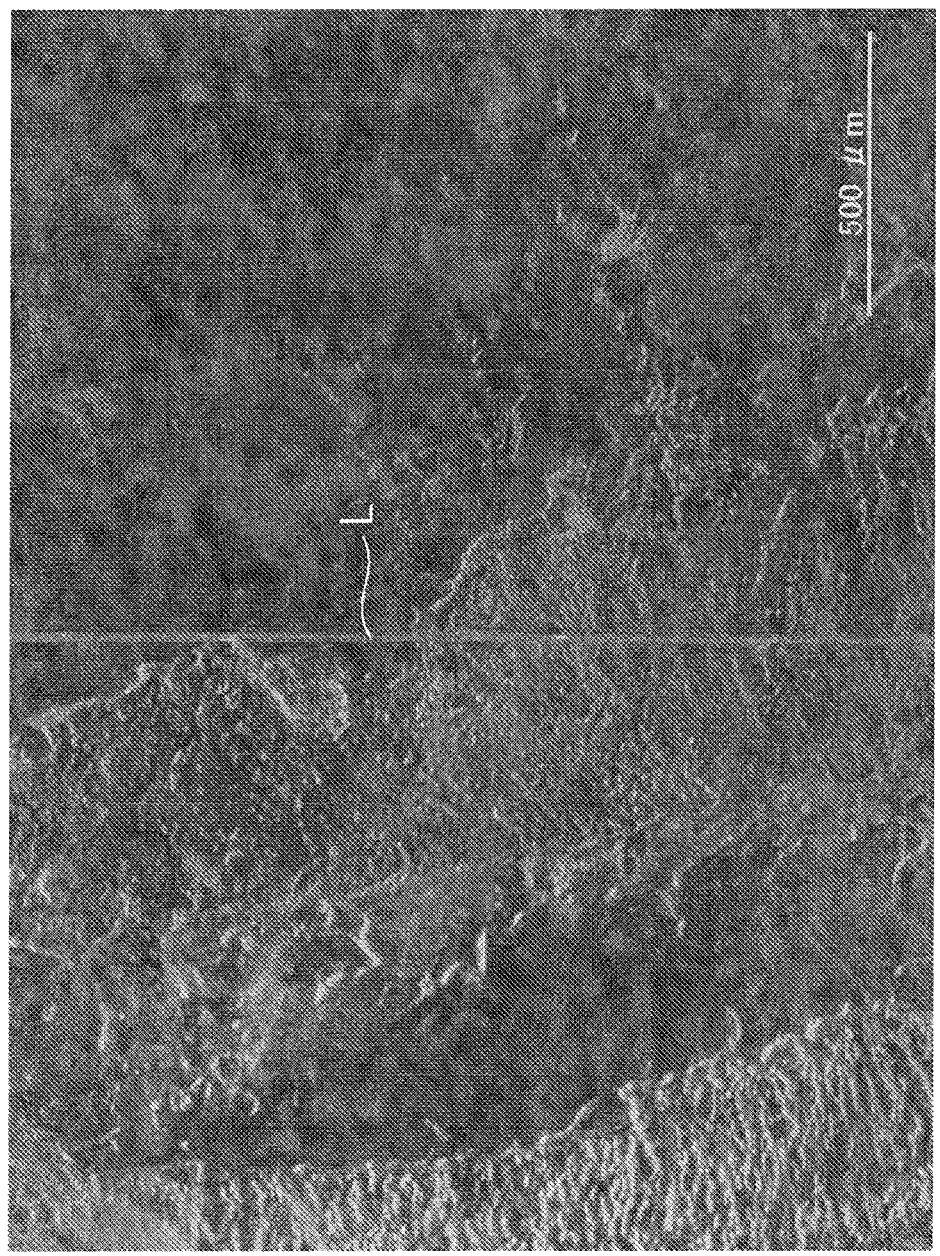
{FIG. 17}

FIG. 17 shows a state before expanding the dicing tape. The line L seen in the vertical direction in the approximate middle of the photograph is the border (dividing line) between the cover glasses.

Figure 18:
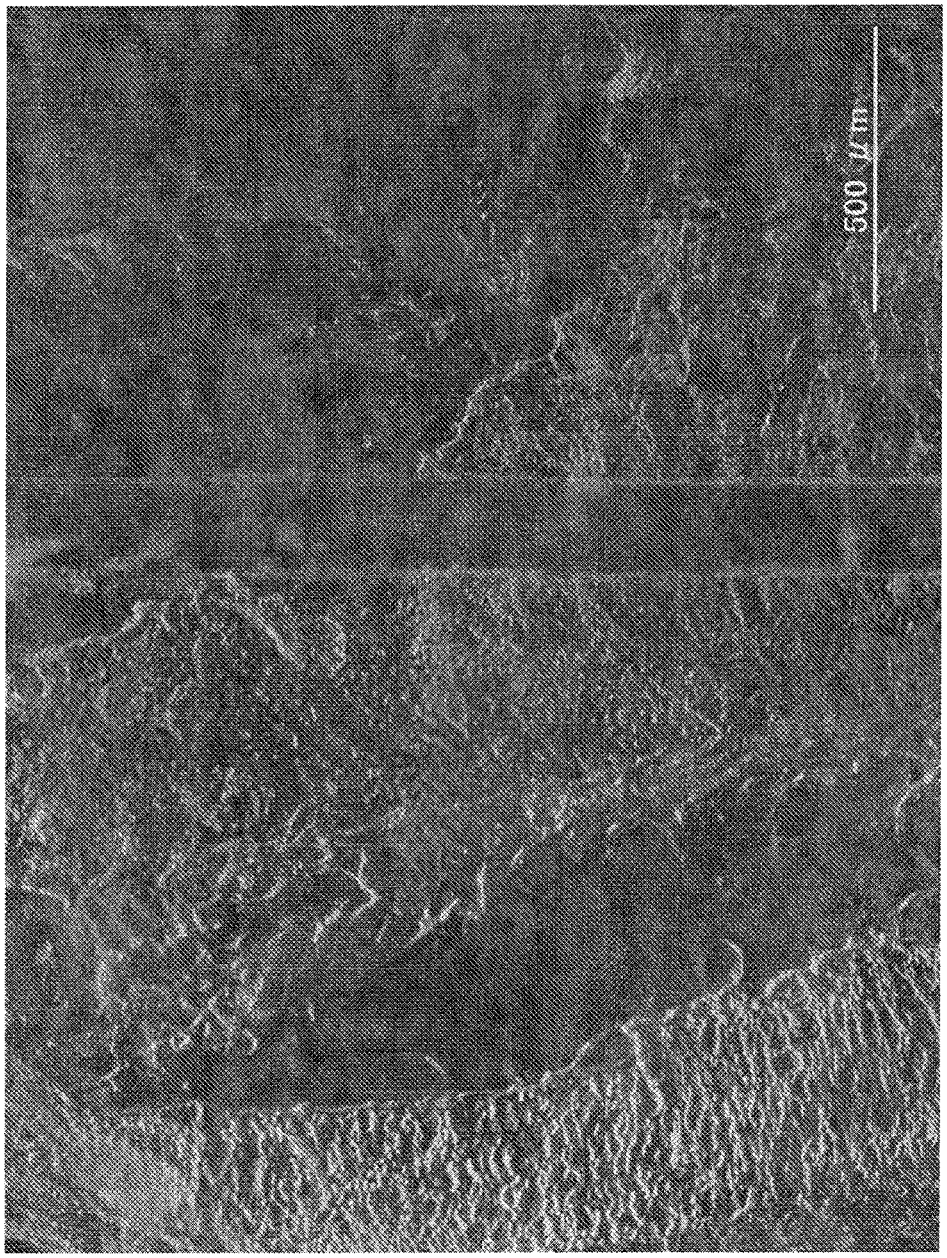
{FIG. 18}

FIG. 18 shows the state after expanding the dicing tape. It was found that the section was sharply divided along the border between the cover glasses.

From the above-mentioned experiment, it was confirmed to be possible, by using the cell collection apparatus and the cell collecting system of the present invention, to easily divide a section sufficiently sharply along the dividing line, even though the thickness is relatively thick.

REFERENCE SIGNS LIST

1 Cell collection apparatus
2 Optical microscope (Observation device)
2a Camera port
2b Specimen stage
3 Imaging device
4 Glass substrate (Substrate)
4a Groove (Dividing line)
4b Small piece
5 Sticky sheet (Expandable member)
6 Expanding stage (Expansion unit, Pressing member)
7 Jig
8 Pickup unit
9a Bottom frame (Fixing member)
9b Top frame
9c and 9d Windows
10a Grip ring, Outer ring (Holding member)
10b Grip ring, Inner ring (Holding member)
10c Grip ring, Top ring (Holding member)
10d Grip ring, Bottom ring (Holding member)
11 Pickup needle (Needle member)
12 Manipulator
12a Arm
13 Tube rack
13a Collection tube
14a Outer cylinder
14b Inner cylinder
15 Fixing member
16 Holder
17 Needle assembly member
18 Flat plate
19 Suction member
21 Needle
22 Funnel-shaped guide member
23 Collection container
24 Observation unit
100 Cell collecting system

What is claimed is:

1. A cell collecting method comprising:
   (a) pasting a section of a biological tissue on a surface of a substrate that is configured to be divided into a plurality of small pieces along a predetermined dividing line, while having the section bridged over the dividing line;
   (b) determining which of a small piece of substrate with a section of the biological tissue pasted thereon to pick up based on a shape of the biological tissue or a distribution of cells in the biological tissue;
   (c) dividing the substrate and the section of the biological tissue along the dividing line, by expanding the substrate pasted with the section in a direction along the surface, to form the small piece of substrate with a section of biological tissue pasted thereon; and
   (d) picking up one or more small pieces of the section that has been divided in the step (c) and determined for pick up in step (b).

2. The cell collecting method of claim 1, wherein the substrate comprises a plurality of separated pieces adhered to the expandable member in mutually adjacent and aligned state.

3. The cell collecting method of claim 1, wherein the dividing line is composed of a groove formed in the surface of the substrate.

4. The cell collecting method of claim 1, wherein the substrate is adhered in a detachable matter to an expandable member.

5. The cell collecting method of claim 4, wherein the expandable member has stickiness on its surface.

6. The cell collecting method of claim 4, wherein the expandable member comprises an optically transparent or semi-transparent material.

7. The cell collecting method of claim 4, wherein the expandable member expands circumferentially from a point of the expandable member that is adhered to the substrate.

8. The cell collecting method of claim 4, wherein at least one of the plurality of the small pieces and portion of biological tissue pasted thereon are detached and picked up from the expandable member.

9. The cell collecting method of claim 8, wherein a needle member detaches at least one of the plurality of the small pieces and portion of biological tissue pasted thereon by pushing a position of the expandable member being adhered with the small pieces, from the surface on the opposite side to the surface adhered with the small pieces.

10. The cell collecting method of claim 8, wherein a suction member adheres by suction to and picks up at least one of the plurality of small pieces from the surface of the expandable member where the substrate is adhered.

11. The cell collecting method of claim 1, wherein each of the plurality of small pieces is in a cuboid-shape having a thickness of 0.05 to 0.5 mm and side lengths of 0.05 to 5.0 mm.

12. A cell collecting method comprising:
    (a) pasting a section of a biological tissue on a surface of a substrate that is configured to be divided into a plurality of small pieces along a predetermined dividing line, while having the section bridged over the dividing line;
    (b) acquiring an analyte section image;
    (c) staining a portion of the biological tissue, forming a stained section;
    (d) acquiring a stained-section image;
    (e) overlaying the analyte section image with the stained-section image to form an overlay image;
    (f) determining from the overlay image which of the small pieces with biological tissue pasted thereon to pick up;
    (g) dividing the substrate and the section of the biological tissue along the dividing line, by expanding the substrate pasted with the section in a direction along the surface, to form a small piece of substrate with a section of biological tissue pasted thereon; and
    (h) picking up one or more small pieces of the section that has been divided in step (g) and determined for pick up in step (f).

* * * * *